US009970066B2

(12) United States Patent
Barker et al.

(10) Patent No.: US 9,970,066 B2
(45) Date of Patent: May 15, 2018

(54) METHOD OF DETECTING *COCCIDIOIDES* SPECIES

(71) Applicants: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

(72) Inventors: Bridget Barker, Flagstaff, AZ (US); Elizabeth Driebe, Flagstaff, AZ (US); David Engelthaler, Flagstaff, AZ (US); Paul Keim, Flagstaff, AZ (US); Jolene Bowers, Flagstaff, AZ (US)

(73) Assignees: The Translational Genomics Research Institute, Phoenix, AZ (US); Arizona Board of Regents on behalf of Northern Arizon University, Flagstaff, AZ (US)

( * ) Notice: Subject to any disclaimer, the term of this patent is extended or adjusted under 35 U.S.C. 154(b) by 0 days. days.

(21) Appl. No.: 15/224,044

(22) Filed: Jul. 29, 2016

(65) Prior Publication Data

US 2016/0326603 A1 Nov. 10, 2016

Related U.S. Application Data

(63) Continuation-in-part of application No. 13/935,668, filed on Jul. 5, 2013, now Pat. No. 9,404,161.

(60) Provisional application No. 61/668,203, filed on Jul. 5, 2012, provisional application No. 62/319,612, filed on Apr. 7, 2016.

(51) Int. Cl.

| | |
|---|---|
| ***C12Q 1/68*** | (2006.01) |
| ***C07H 21/02*** | (2006.01) |
| ***C07H 21/04*** | (2006.01) |

(52) U.S. Cl.

CPC ...... *C12Q 1/6895* (2013.01); *C12Q 2600/112* (2013.01); *C12Q 2600/16* (2013.01)

(58) Field of Classification Search

None

See application file for complete search history.

(56) References Cited

U.S. PATENT DOCUMENTS

| | | | | |
|---|---|---|---|---|
| 9,404,161 B2 * | 8/2016 | Engelthaler | .......... | C12Q 1/6895 |
| 2014/0011693 A1 * | 1/2014 | Engelthaler | .......... | C12Q 1/6895 506/9 |

* cited by examiner

*Primary Examiner* — Carla J Myers

(74) *Attorney, Agent, or Firm* — Rodney J. Fuller; Booth Udal Fuller, PLC

(57) ABSTRACT

The present technology provides methods and kits that may be used to detect and quantify the presence of *Coccidioides* species. The methods include quantification real-time PCR assays, and the kits and compositions include oligonucleotides used as primers and probes.

26 Claims, No Drawings

METHOD OF DETECTING *COCCIDIOIDES* SPECIES

CROSS-REFERENCE TO RELATED APPLICATIONS

This application is a Continuation-In-Part of U.S. patent application Ser. No. 13/935,668, filed Jul. 5, 2013 (published as US 20140011693), which claims the benefit of U.S. Provisional Application No. 61/668,203, filed Jul. 5, 2012; this application also claims the benefit of U.S. Provisional Application No. 62/319,612, filed Apr. 7, 2016. The entire contents and disclosure of the above-mentioned applications are herein incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 8 kilobyte ASCII (text) file named "Seq_list" created on Jul. 15, 2016.

FIELD OF THE TECHNOLOGY

The present technology provides methods and kits for specifically detecting and quantifying *Coccidioides* in a sample, including an environmentally derived sample, such as soil.

BACKGROUND OF THE TECHNOLOGY

Coccidioidomycosis is caused by infection with *Coccidioides immitis* or *Coccidioides posadasii* (collectively "*Coccidioides*"). *C. immitis* and *C. posadasii* are the fungal etiologic agents of coccidioidomycosis (a.k.a. Valley Fever) and are endemic to arid soils of the southwest United States, as well as parts of Mexico, and Central and South America. Primary hosts acquire *Coccidioides* via inhalation of aerosolized arthroconidia upon soil disruption. Coccidioidomycosis most commonly causes a progressive pulmonary infection in humans and other vertebrate hosts but also can disseminate to other body parts including the skin, brain, bone, and meninges. This disseminated secondary coccidioidomycosis often is severe and can result in patient death. However, in cases where infection is resolved, patients usually acquire a specific and lifelong immunity to the fungus.

Coccidioidomycosis infection rates have increased dramatically in the last decade with the State of Arizona documenting the number of reported cases per 100,000 people having increased from 20.8 in 1997 to 186.0 in 2010. Increased physician awareness and testing likely accounts for a portion of this case increase. An additional cause for this increase may be influxes of immunologically naïve individuals into Arizona. A significant number of individuals from outside the *Coccidioides* endemic region migrate annually to the desert southwest and are at greater risk for developing coccidioidomycosis, even after returning to their respective homes. These infections, therefore, are likely to escape or confound diagnosis in non-endemic regions.

While Real-Time PCR based assays have been developed that can help clinicians identify *Coccidioides* as a cause of illness, these assays have lacked needed sensitivity and do not accurately quantify the load of *Coccidioides* organisms in an infection.

BRIEF SUMMARY OF THE TECHNOLOGY

Provided herein is a method of determining the presence or absence of *Coccidioides* in a DNA-containing sample. The general method comprises the steps of: (1) adding a first and a second oligonucleotide capable of binding SEQ ID NO. 1 to a mixture comprising the DNA-containing sample, wherein the first oligonucleotide includes at least one sequence selected from the group consisting of SEQ ID NOs: 10-20 and oligonucleotides having at least 90% sequence identity to any one of SEQ ID NOs: 10-20, wherein the second oligonucleotide includes at least one sequence selected from the group comprising SEQ ID NOs: 21-38, and oligonucleotides having at least 90% sequence identity to any one of SEQ ID NOs: 21-38. The method may also include (2) subjecting the mixture containing the first and second oligonucleotides to conditions that allow amplification of nucleic acid comprising the first oligonucleotide, (3) obtaining a result indicating nucleic acid amplification comprising the first oligonucleotide; and (4) determining the presence or absence of *Coccidioides* in the DNA-containing sample based on the result. In some examples, the result obtained by the general method comprises a Ct value. The general method as set forth above may further comprise the step of adding a third oligonucleotide to the mixture, wherein the third oligonucleotide binds to its complement included in the amplification products by the first and second oligonucleotides. The third oligonucleotide preferably includes a sequence selected from the group consisting of SEQ ID NO. 2 and homologs thereof having at least 90% sequence identity and complementarity under similar stringency. In the general method, at least one of the first, the second and the third oligonucleotides comprises a label. For some examples, the label may comprise a fluorescent label selected from the group consisting of FAM, dR110, 5-FAM, 6FAM, dR6G, JOE, HEX, VIC, TET, dTAMRA, TAMRA, NED, dROX, PET, BHQ+, Gold540, MGB-NFQ, and LIZ. In one example, the third oligonucleotide comprises a fluorescent label selected from the group consisting of FAM, dR110, 5-FAM, 6FAM, dR6G, JOE, HEX, VIC, TET, dTAMRA, TAMRA, NED, dROX, PET, BHQ+, Gold540, MGB-NFQ, and LIZ. In some preferred embodiments, when at least one, two or all of the first, second, and third oligonucleotides include labels, the labels are preferably different for the at least two and preferably for all of the first, second, and third oligonucleotides, respectively.

The general method as provided may further comprise the step of isolating DNA from the DNA-containing sample. The sample may comprise an environmental sample or may be derived from a subject. In preferred forms, the subject is selected from the group consisting of a human, a companion animal, a livestock animal, and a wild animal species. In other preferred aspects, the environmental sample may be a soil sample.

Also provided is a method of quantifying *Coccidioides* in a DNA-containing sample. The method may comprise the steps of: (1) adding a first and a second oligonucleotide capable of binding SEQ ID NO. 1 to a mixture comprising the DNA-containing sample, wherein the first oligonucleotide includes at least one sequence selected from the group consisting of SEQ ID NOs: 10-20 and oligonucleotides having at least 90% sequence identity to any one of SEQ ID NOs: 10-20, wherein the second oligonucleotide includes at least one sequence selected from the group comprising SEQ ID NOs: 21-38, and oligonucleotides having at least 90% sequence identity to any one of SEQ ID NOs: 21-38; (2) subjecting the mixture containing the first and second oligonucleotides to conditions that allow amplification of a template DNA comprising the first oligonucleotide; (3) obtaining a first result indicating amplification of the template DNA and *Coccidioides* quantification; and (4) calculating *Coccidioides* quantification based on the first result in comparison to a reference result, wherein *Coccidioides* quantification determines the amount of template DNA in the sample. In some example, the reference result is obtained by the same quantification method using a DNA-containing sample having a known quantity of *Coccidioides*. In some other example, the reference result is predetermined. Sometimes, each of the first and the reference result comprises a Ct value.

The quantification method may further comprise the step of adding a third oligonucleotide to the mixture, wherein the third oligonucleotide binds to its complement included in the amplification products by the first and second oligonucleotides. In one example, the third oligonucleotide includes a sequence selected from the group consisting of SEQ ID NO. 2 and homologs thereof having at least 90% sequence identity and complementarity under similar stringency. In the quantification method, at least one of the first and the second oligonucleotides comprises a label. In some preferred forms, if more than one of the first, second, or third oligonucleotides are used and more than one of these includes a label, the labels will be different for the first, second, and third nucleotides, respectively. In some examples, the label comprises a fluorescent label selected from the group consisting of FAM, dR110, 5-FAM, 6FAM, dR6G, JOE, HEX, VIC, TET, dTAMRA, TAMRA, NED, dROX, PET, BHQ+, Gold540, MGB-NFQ, and LIZ. In one example, the third oligonucleotide comprises a fluorescent label selected from the group consisting of FAM, dR110, 5-FAM, 6FAM, dR6G, JOE, HEX, VIC, TET, dTAMRA, TAMRA, NED, dROX, PET, BHQ+, Gold540, MGB-NFQ, and LIZ.

The quantification method may further comprise the step of isolating DNA from the DNA-containing sample. In some examples, the sample comprises an environmental sample. In other examples, the sample is derived from a subject, preferably the subject is selected from the group consisting of a human, a companion animal, and a livestock animal. In some additional embodiments, the environmental sample may comprise a soil sample.

Other aspects and iterations of the technology are described in more detail below.

DETAILED DESCRIPTION OF THE TECHNOLOGY

The present technology discloses assays, methods and kits designed to detect and quantify total *Coccidioides* sp in a sample. This technology provides a genomic target specific to *Coccidioides* sp, including *C. immitis* and *C. posadasii*, and other *Coccidiodies* species. A real-time quantitative Polymerase Chain Reaction (real-time qPCR) based assay, providing a straightforward, highly sensitive and specific assay system for rapidly detecting and quantifying *Coccidioides* in a sample, is provided based on the genomic target disclosed herein.

I. Species or Strain Specific Sequences

Species or strain specific sequences are sequences unique to the species or strain, that is, not shared by other previously characterized species or strains. The species specific sequences identified in *C. immitis* and *C. posadasii* often differ only by a single nucleotide, which is called SNP (single nucleotide polymorphism). The strain specific SNP, is also called allelic identification herein, signifies the identity of *C. immitis* or *C. posadasii*. The concept of "allele" or "allelic" is detailed below.

When a particular species or strain specific sequence is identified, probes or primers may be designed based on any part of that sequence. The probes or primers may also be the entirety of that sequence. The primers or probes designed according to a particular species or strain sequence, or alleles thereof, may also be represented in degenerate form, or comprise chemically modified nucleic acids, or any other components that facilitate the identification of the identifying sequence of a strain or species. The concept of a sequence identified to be specific to a species or strain further encompasses nucleic acid sequences that are less than 100% identical to the specific sequence, but are still capable of specifically detecting the species or strain. Note that in a nucleic acid sequence, T or U may be used interchangeably depending on whether the nucleic acid is DNA or RNA. A sequence having less than 60% 70%, 80%, 90%, 95%, 99% or 100% identity to the identifying sequence or allele thereof may still be encompassed by the technology if it is capable of binding to its complementary sequence and/or facilitating nucleic acid amplification of a desired target sequence.

As used herein, the term "sample" may refer to any source in which *Coccidioides* nucleic acids may be detectable. A sample may be derived from anywhere that fungus or any part of a fungal body may be found including soil, air, water, solid surfaces (whether natural or artificial) culture media, foodstuffs, and any interfaces between or combinations of these elements. Additionally, a sample may be derived from a subject, such as a plant or animal, including humans. Samples derived from animals include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. Samples derived from subjects may also take the form of a fluid sample such as peripheral blood, lymph fluid, ascites, serous fluid, pleural effusion, sputum, bronchial wash, bronchioalveolar lavage fluid (BALF), cerebrospinal fluid, semen, amniotic fluid, lacrimal fluid, stool, urine, hair, or any other source in which a fungus, or any part of a fungus might be present. Samples collected from a plant may be collected from part of a plant or from an entire plant. Samples may be collected by any method now known or yet to be disclosed, including swiping or swabbing an area or orifice, removal of a piece of tissue as in a biopsy, or any method known to collect bodily fluids. Samples may also include *Coccidioides* that has been previously isolated from one or more prior samples and grown in an isolated environment (e.g., a laboratory). Thereafter, one or more biomolecules (e.g., nucleic acids or protein) can be isolated from the *Coccidioides* for used in the methods disclosed herein.

An allele includes any form of a particular nucleic acid that may be recognized as a form of existence of a particular nucleic acid on account of its location, sequence, modification, or any other characteristics that may identify it as being a particular existing form of that particular nucleic acid. Alleles include, but need not be limited to, forms of a nucleic acid that include point mutations, deletions, single nucleotide polymorphisms (SNPs), inversions, translocations, heterochromatic insertions, and differentially methylated sequences relative to a reference gene, whether alone or in combination. When a particular nucleic acid is a gene, the allele of this particular gene may or may not produce a functional protein; the functional protein thereof may or may not comprise a silent mutation, or frame-shift mutation. The different alleles of a particular gene may each produce a protein with altered function, localization, stability, dimerization, or protein-protein interaction; and may have overexpression, under-expression or no expression; may have altered temporal or spatial expression specificity. The presence or absence of an allele may be detected through the use of any process known in the art, including using primers and probes designed accordingly for PCR, sequencing, hybridization analyses. An allele may also be called a mutation or a mutant. An allele may be compared to another allele that may be termed a wild type form of an allele. In some cases, the wild type allele is more common than the mutant.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an inducing agent such as DNA polymerase and at a suitable temperature and pH. The primer is preferably single-stranded for maximum efficiency in amplification. Alternatively, the primer is first treated to ensure that it is single-stranded before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. Oligonucleotides, such as a probe or primer, containing a sequence complementary to a sequence specific to a *Coccidioides* species or strain will typically not hybridize to the corresponding portion of the genome of other species or strains under stringent conditions. Understood by those skilled in the art, for example, high stringent hybridization conditions are equivalent to: 5×SSPE, 0.5% SDS, 5×Denhardt's reagent and 100 μg/ml denatured salmon sperm DNA at 42° C. followed by washing in a solution comprising 0.1×SSPE, 1.0% SDS at 42° C. when a probe of about 500 nucleotides in length is employed, and washed with 2×SSC, 0.1% SDS followed by 0.1×SSC, 0.1% SDS. Stringent conditions in PCR reaction may be controlled by temperature or by the concentration of certain salt in the buffer.

Primers and probes that are designed based on strain specific genes, allelic discriminative nucleic acid, or alleles thereof, are often used to screen samples to specifically and selectively detect the presence or absence of a particular species or strain of a bacteria, fungus, virus, or a pathogen thereof. The detection using primers and probes may be through various methods including PCR-based (polymerase chain reaction-based) methods such as real-time PCR, quantitative PCR, quantitative real time PCR; allele specific ligation; comparative genomic hybridization; sequencing; and other methods known in the art. One aspect of the present technology provides primers based on *Coccidioides* specific sequence for quantitative PCR assays comprising one or more specific primer sets and probes to detect the presence of *Coccidioides* DNA.

When a nucleic acid includes a particular sequence, the sequence may be a part of a longer nucleic acid or may be the entirety of the sequence. The nucleic acid may contain nucleotides 5' of the sequence, 3' of the sequence, or both. The concept of a nucleic acid including a particular sequence further encompasses nucleic acids that contain less than the full sequence that are still capable of specifically detecting a marker. Nucleic acid sequences may be identified by the IUAPC letter code which is as follows: A—Adenine base; C—Cytosine base; G—guanine base; T or U—thymine or uracil base. For some degenerate primers or oligonucleotides, the following abbreviations may be used to provide sequence information: M-A or C; R-A or G; W-A or T; S-C or G; Y-C or T; K-G or T; V-A or C or G; H-A or C or T; D-A or G or T; B-C or G or T; N or X-A or C or G or T. Note that T or U may be used interchangeably depending on whether the nucleic acid is DNA or RNA.

As to probes, they may be used for single probe analysis or multiplex probe/primer combined Real Time PCR and quantitative PCR (qPCR) analysis. Oligonucleotide probes complementary to a selected sequence within the target sequence defined by the amplification region by the primers may be designed. In one exemplary example, oligonucleotide probes facilitating Real Time-PCR/qPCR product detection are complementary to a selected sequence within the target sequence downstream from either the upstream or downstream primer. Therefore, these probes hybridize to an internal sequence of the amplified fragment of a targeted sequence.

Many assays detecting the presence of a target can also quantify the amount of the target in a given sample. In particular, when there is only one copy of the identified strain specific genes, alleles thereof, or other allelic discriminative nucleic acid in a fungal genome, the primers and probes designed to specifically and selectively detect the presence or absence of such single copy target may be further used to quantify the amount of *Coccidioides* spp in a sample. In one embodiment, the *Coccidioides* quantitative diagnosis assay ("CocciDxQ" hereafter) as provided herein is used to quantify *Coccidioides* via a region that is associated with copia-like retrotransposon family protein found in *Coccidioides posadasii* C735 delta SOWgp (GenBank Accession XM 003069703.1; SEQ ID NO:1—TGTTAGGTAATCCAACTAGCACCTCGCTCACGTGACCCACATAGATTAGCCGAGATT CCCCTTTAGGTAGCTTAGTGAATGACAAGCATACAAGTCCTCCATCA) specific to *Coccidioides* species.

In some embodiments, the copia-like retrotransposon family protein found in *Coccidioides posadasii* C735 delta SOWgp (SEQ ID NO: 1) can be employed with additional assays. For example, some embodiments provide an assay that can be used to detect *Coccidioides* in samples, such as a soil sample or a sample derived from a non-environmental source (hereinafter "CocciENV"). For example, CocciENV can be used to detect the presence of one or more species of *Coccidioides* in a soil sample for any downstream purposes, such as establishing an area of endemic Valley Fever. In other embodiments, CocciENV can be used for diagnostic or any other purposes desired by the user.

In some embodiments, the CocciDxQ assay is a real-time PCR that employs a probe and a multiplex set of forward primers and reverse primers that target part or all of the target sequence represented by SEQ ID NO: 1. In one embodiment, the probe is labeled with fluorescence. In another embodiment, the probe comprises a 6FAM and an MGB-NFQ label. In one embodiment the probe comprises a sequence represented by SEQ ID NO: 2 or homologs of SEQ ID NO: 2 with at least 80%, more preferably 90%, still more preferably 91%, even more preferably 92%, still more preferably 93%, even more preferably 94%, still more preferably 95%, even more preferably 96%, still more preferably 97%, even more preferably 98%, still more preferably 99%, and most preferably 99.8% or more identity and complementarity under similar stringency. In one embodiment, the CocciDxQ assay as disclosed herein comprises at least one forward primer and at least one reverse primer comprising primer sequences represented by SEQ ID NOs in Table 1 or homologs of SEQ ID NOs in Table 1 with at least 80% more preferably 90%, still more preferably 91%, even more preferably 92%, still more preferably 93%, even more preferably 94%, still more preferably 95%, even more preferably 96%, still more preferably 97%, even more preferably 98%, still more preferably 99%, and most preferably 99.8% or more identity and complementarity under similar stringency. In one embodiment, the forward primers comprise one or more degenerative primers. In another embodiment, the reverse primers comprise one or more degenerative primers. In yet another embodiment, both the forward primers and the reverse primers comprise one or more degenerative primers. In some embodiments, the CocciDxQ assay may comprise more than 1 forward primer and more than 1 reverse primer. For example, the CocciDxQ assay may comprise two, three, four and more primers; as such, the CocciDxQ assay may comprise two forward primers and one reverse primer, or two forward primers and two reverse primers, or three forward primers and one reverse primer. In one embodiment, the CocciDxQ assay comprises three forward primers and four reverse primers represented by SEQ ID NOs: 3-9 (Table 1).

TABLE 1

| CocciDxQ Assay | | |
|---|---|---|
| Probe Name | Probe Sequence 5' to 3' | SEQ ID NO |
| CQ_3_probe | ACCCACATAGATTAGC | SEQ ID NO: 2 |
| Forward Primer Name | Forward Primer Sequence 5' to 3' | |
| CQ_3_F_v2a | GTGTTAGGTAGTCCAACTAGCACCT | SEQ ID NO: 3 |
| CQ_3_F_v2b | GTGTTAGGTAATCCAACCAGCACCT | SEQ ID NO: 4 |
| CQ_3_F_v2c | GTGTTAGGTAATCCAACTAGCACCT | SEQ ID NO: 5 |
| Reverse Primer Name | Reverse Primer Sequence 5' to 3' | |
| CQ_3_R_v2a | CTGATGGAGGACTCGTATGCTTGT | SEQ ID NO: 6 |
| CQ_3_R_v2b | CTGATGGAGGACTTGTACACTTGT | SEQ ID NO: 7 |
| CQ_3_R_v2c | CTGATGGAGGAATTGTATGCTTGT | SEQ ID NO: 8 |
| CQ_3_R_v2d | CTGATGGAGGACTTGTATGCTTGT | SEQ ID NO: 9 |

The provided assays can detect less than one genomic DNA molecule per microliter of DNA, which sensitivity is imparted by high genomic copy number of the target gene, 85 copies/genome.

In some embodiments, the CocciENV assay is a real-time PCR that employs a probe and a multiplex set of forward primers and reverse primers that target part or all of the target sequence represented by SEQ ID NO: 1. In one embodiment, the probe is labeled with fluorescence. In another embodiment, the probe comprises a 6FAM and an MGB-NFQ label. In one embodiment the probe comprises a sequence represented by SEQ ID NO: 2 or homologs of SEQ ID NO: 2 with at least 80%, more preferably 90%, still more preferably 91%, even more preferably 92%, still more preferably 93%, even more preferably 94%, still more preferably 95%, even more preferably 96%, still more preferably 97%, even more preferably 98%, still more preferably 99%, and most preferably 99.8% or more identity and complementarity under similar stringency. In one embodiment, the CocciENV assay as disclosed herein comprises at least one forward primer and at least one reverse primer comprising primer sequences represented by SEQ ID NOs in Table 2 or homologs of SEQ ID NOs in Table 2 with at least 80% more preferably 90%, still more preferably 91%, even more preferably 92%, still more preferably 93%, even more preferably 94%, still more preferably 95%, even more preferably 96%, still more preferably 97%, even more preferably 98%, still more preferably 99%, and most preferably 99.8% or more identity and complementarity under similar stringency.

In one embodiment of the CocciENV assay, the forward primers comprise one or more degenerative primers. In another embodiment of the CocciENV assay, the reverse primers comprise one or more degenerative primers. In yet another embodiment CocciENV assay, both the forward primers and the reverse primers comprise one or more degenerative primers. In some embodiments, the CocciENV assay may comprise more than 1 forward primer and more than 1 reverse primer. For example, the CocciENV assay may comprise two, three, four and more primers; as such, the CocciENV assay may comprise two forward primers and one reverse primer, or two forward primers and two reverse primers, or three forward primers and one reverse primer. In one embodiment, the CocciENV assay comprises a plurality of forward primers and a plurality of reverse primers represented by SEQ ID NOs: 10-38 (Table 2).

TABLE 2

| CocciENV Assay | | |
|---|---|---|
| Probe Name | Probe Sequence 5' to 3' | SEQ ID NO |
| CQ_3_probe | ACCCACATAGATTAGC | SEQ ID NO: 2 |
| Forward Primer Name | Forward Primer Sequence 5' to 3' | |
| CocciEnv_F1d1 | CGTTGCACRGGGAGCACCT | SEQ ID NO: 10 |
| CocciEnv_F2 | AAGCTTTGGATCTTTGTGGCTCT | SEQ ID NO: 11 |
| CocciEnv_F3 | AATTGATCCATTGCAAGCACCT | SEQ ID NO: 12 |
| CocciEnv_F4 | AATCCAACCTTTGGAACTACACCT | SEQ ID NO: 13 |
| CocciEnv_F5 | TTTTCCGGTATGGACTAGCACCT | SEQ ID NO: 14 |
| CocciEnv_F6d2 | TGTTAGGTAATCYAACYAGCACCT | SEQ ID NO: 15 |
| CocciEnv_F7d2 | TRTTAGGTAATYCAACTAGCACCT | SEQ ID NO: 16 |
| CocciEnv_F8d1 | TGTTAGATAATCCAACYAGCACCT | SEQ ID NO: 17 |
| CocciEnv_F9d2 | GKTARGTAATCCAACTAGCACCT | SEQ ID NO: 18 |
| CocciEnv_F10d2 | TGTTAGGTARTCCAACTAGCAYCT | SEQ ID NO: 19 |
| CocciEnv_F11d2 | TGTTAGGTAATCCAACTMGCACYT | SEQ ID NO: 20 |
| Reverse Primer Name | Reverse Primer Sequence 5' to 3' | |
| CocciEnv_R1 | GATGGAGGACTCTATATGCTTGT | SEQ ID NO: 21 |
| CocciEnv_R2 | ATGGAGGACTCGTTATGCCTGT | SEQ ID NO: 22 |
| CocciEnv_R3 | GGAGGACCCGTATGCTTGTGT | SEQ ID NO: 23 |
| CocciEnv_R4 | TGCTAAATGATGGAGGGCTTGT | SEQ ID NO: 24 |
| CocciEnv_R5 | GATGGAGGCTCGTATGCTTGT | SEQ ID NO: 25 |
| CocciEnv_R6 | AAGGGGTTTGTGGTGAATCCTTA | SEQ ID NO: 26 |
| CocciEnv_R7 | CAGAAAAATAGCCGTATGCTTGT | SEQ ID NO: 27 |
| CocciEnv_R8d2 | TRATGGAGRACTTGTATGCTTGT | SEQ ID NO: 28 |
| CocciEnv_R9d1 | TGATGGAGGACTCGTATGCYTGT | SEQ ID NO: 29 |
| CocciEnv_R10d2 | TGATGGARRACTCATATGCTTGT | SEQ ID NO: 30 |
| CocciEnv_R11d2 | TGATAGAGAACTTGTATRCTTRT | SEQ ID NO: 31 |
| CocciEnv_R12d2 | TGATGAAGAACTTRTATRCTTGT | SEQ ID NO: 32 |
| CocciEnv_R13d2 | TGATRRAGGACTTGTATGCTTGT | SEQ ID NO: 33 |
| CocciEnv_R14 | TGATGGAAAACTTGTATGCTTGT | SEQ ID NO: 34 |
| CocciEnv_R15d2 | TGATGGAGGACTTGTAYAYTTGT | SEQ ID NO: 35 |
| CocciEnv_R16d2 | TGATGGAGGACTTGTAYGCTTRT | SEQ ID NO: 36 |
| CocciEnv_R17d2 | TGATGGAGGACTYATATGCTTRT | SEQ ID NO: 37 |
| CocciEnv_R18d2 | GATGGAGGACTCGTWYGCTTGT | SEQ ID NO: 38 |

Further illustrations of various aspects of the technology are detailed below.

II. Methods for Detecting *Coccidioides* Using Species Specific Genomic Target Sequences Methods that can be used to identify strain or species specific nucleic acids and alleles thereof, and biomarkers derived from transcriptional and translational products of the strain or species specific nucleic acids and the alleles thereof, include PCR, Real-Time PCR, hybridization, sequencing and any combination of the above methods. In one embodiment, the presence of the PCR or Real-Time PCR products in an assay may indicate the presence of *Coccidioides* species or one or more strains thereof. In one embodiment, the PCR or Real Time-PCR products may be further identified or differentiated by hybridization performed either simultaneously with or subsequently to the PCR reactions. In another embodiment, the PCR or Real-Time PCR products may be sequenced to ascertain the existence of a particular allele indicative of the identity of *Coccidioides* species or one or more strains thereof in a sample.

A nucleic acid may be added to a sample by any of a number of methods, including manual methods, mechanical methods, or any combination thereof. The presence of the allele may be signified by any of a number of methods, including amplification of a specific nucleic acid sequence, sequencing of a native or amplified nucleic acid, or the detection of a label either bound to or released from the nucleic acid. Addition of the nucleic acid to the sample also encompasses a sample absent of the target allele to which the nucleic acid has specificity.

Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3 SR), nucleic acid sequence based amplification (NASBA), strand displacement amplification (SDA), amplification with Qβ replicase, whole genome amplification with enzymes such as φ29, whole genome PCR, in vitro transcription with Klenow or any other RNA polymerase, or any other method by which copies of a desired sequence are generated.

With PCR, it is possible to amplify a single copy of a specific target sequence in genomic DNA to a level detectable by several different methodologies, such as hybridization with a labeled probe; incorporation of biotinylated primers followed by avidin-enzyme conjugate detection; incorporation of $^{32}$P-labeled deoxynucleotide triphosphates—dCTP or dATP—into the amplified segment. In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTPs). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent) stain, enzyme, or nonradioactive metal. Specific examples include, but are not limited to: fluorescein, biotin, digoxigenin, alkaline phosphatese, biotin, streptavidin, $^{3}$H, $^{14}$C, $^{32}$P, $^{35}$S, or any other compound capable of emitting radiation, rhodamine, 4-(4'-dimethylamino-phenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR.

Either primers or primers along with probes, as described above, will allow a quantification of the amount of specific template DNA present in the initial sample. In addition, RNA may be detected by PCR analysis by first creating a DNA template from RNA through a reverse transcriptase enzyme. In some aspects of the technology, the allele may be detected by quantitative PCR analysis facilitating genotyping analysis of the samples.

An illustrative example, using dual-labeled oligonucleotide probes in PCR reactions is disclosed in U.S. Pat. No. 5,716,784 to DiCesare. In the PCR step of the multiplex Real Time-PCR/PCR reaction of the present technology, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g. Applied Biosystems™ 7900HT real-time PCR platform (Applied Biosystems, Carlsbad, Calif.) and Roche's 480 LightCycler (Roche, Basel, Switzerland), the ABI Prism 7700 sequence detector (Applied Biosystems, Carlsbad, Calif.) using 96-well reaction plates or GENEAMP PC System 9600 or 9700 (Applied Biosystems, Carlsbad, Calif.) in 9600 emulation mode followed by analysis in the ABI Prism Sequence Detector or TAQMAN LS-50B PCR Detection System (Applied Biosystems, Carlsbad, Calif.). The labeled probe facilitated multiplex Real Time-PCR/PCR can also be performed in other real-time PCR systems with multiplexing capabilities.

In some forms of PCR assays, quantification of a target in an unknown sample is often required. Such quantification is often in reference to the quantity of a control sample. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithms.

The algorithm for Ct values in Real-Time PCR calculates the cycle at which individual PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software (Roche, Basel, Switzerland) calculates the second derivatives of entire amplification curves and determines where this value is at its maximum. By using the second-derivative algorithm, data obtained are more reliable and reproducible, even if fluorescence is relatively low.

In addition to PCR, genotyping analysis may also be performed using a probe that is capable of hybridizing to a nucleic acid sequence of interest. The term "hybridization" refers to the pairing of complementary nucleic acids. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids. A single molecule that contains pairing of complementary nucleic acids within its structure is said to be "self-hybridized."

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" when used in relation to nucleic acids refers to a degree of complementarity. There may be partial homology, or complete homology and thus identical. "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence, one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding, or hybridization, of a sequence that is completely homologous to a target under conditions of low stringency. This is not to say that conditions of low stringency are such that non-specific binding is permitted; low stringency conditions require that the binding of two sequences to one another be a specific and selective interaction. The absence of non-specific binding may be tested by the use of a second target which lacks even a partial degree of complementarity, for example, less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 μg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components, for example, the presence or absence of formamide, dextran sulfate, polyethylene glycol, are considered and the hybridization solution may be varied to generate conditions of low stringency hybridization different from, but equivalent to, the above listed conditions. In addition, conditions are known in the art that promote hybridization under conditions of high stringency, for example, increasing the temperature of the hybridization and/or wash steps, the use of formamide in the hybridization solution, etc.

When used in reference to a double-stranded nucleic acid sequence such as a cDNA or genomic clone, the term “substantially homologous” refers to any probe that can hybridize to either or both strands of the double-stranded nucleic acid sequence under conditions of low to high stringency as described above.

When used in reference to a single-stranded nucleic acid sequence, the term “substantially homologous” refers to any probe that can hybridize, or is the complement of, the single-stranded nucleic acid sequence under conditions of low to high stringency as described above.

The term “Tm” refers to the “melting temperature” of a nucleic acid. The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: Tm=81.5+0.41(% G+C), when a nucleic acid is in aqueous solution at 1 M NaCl (See for example, Anderson and Young, Quantitative Filter Hybridization (1985) in Nucleic Acid Hybridization). Other references include more sophisticated computations that take structural as well as sequence characteristics into account for the calculation of Tm.

As used herein the term “stringency” refers to the conditions of temperature, ionic strength, and the presence of other compounds such as organic solvents, under which nucleic acid hybridizations are conducted. With “high stringency” conditions, nucleic acid base pairing will occur only between nucleic acid fragments that have a high frequency of complementary base sequences. Thus, conditions of “low” stringency are often required with nucleic acids that are derived from organisms that are genetically diverse, as the frequency of complementary sequences is usually less.

Probes for hybridization may comprise nucleic acids, oligonucleotides (DNA or RNA), proteins, protein complexes, conjugates, natural ligands, small molecules, nanoparticles, or any combination of molecules that includes one or more of the above, or any other molecular entity capable of specific binding to any allele, whether such molecular entity exists now or is yet to be disclosed. In one aspect of the technology, the probe comprises an oligonucleotide, as described herein.

Under some circumstances, methods of detecting a gene or an allele may involve assessing their expression level through their transcriptional or translational products such as a RNA or protein molecules. The expression of a gene or an allele may be assessed by any of a number of methods used currently in the art and yet to be developed. Examples include any nucleic acid detection method, including the following non-limiting examples, microarray analysis, RNA in situ hybridization, RNAse protection assay, Northern blot. Other examples include any process of detecting expression that uses an antibody including the following non-limiting examples, flow cytometry, immunohistochemistry, ELISA, Western blot, Northwestern blot, and immunoaffinity chromatograpy. Antibodies may be monoclonal, polyclonal, or any antibody fragment, for example, Fab, $F(ab)_2$, Fv, scFv, phage display antibody, peptibody, multi-specific ligand, or any other reagent with specific binding to a target. Other methods of assessing protein expression include the following non-limiting examples: HPLC, mass spectrometry, protein microarray analysis, PAGE analysis, isoelectric focusing, 2-D gel electrophoresis, and enzymatic assays.

In some aspects of the technology, the presence of an allele may be established by binding to probes in a media or on a microarray such as a DNA chip. Examples of DNA chips include chips in which a number of single stranded oligonucleotide probes are affixed to a solid substrate such as silicon glass. Oligonucleotides with a sequence complementary to an allele are capable of specifically binding to that allele to the exclusion of alleles that differ from the specific allele by one or more nucleotides. Labeled sample DNA is hybridized to the oligonucleotides and detection of the label is correlated with binding of the sample, and consequently, the presence of the allele in the sample.

In allele-specific hybridization, oligonucleotide sequences representing all possible variations at a polymorphic site are included on a chip. The chip and sample are subjected to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTPs are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

A nucleic acid probe may be affixed to a substrate. Alternatively, a sample may be affixed to the substrate. A probe or sample may be covalently bound to the substrate or it may be bound by some non-covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi-solid material onto which a probe may be affixed, either singly or in the presence of one or more additional probes or samples as is exemplified in a microarray. Examples of substrate materials include but are not limited to polyvinyl, polystyrene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction. The sample may be bound to a substrate in the case of a Southern Blot.

A nucleic acid probe may include a label. A label may be any substance capable of aiding a machine, detector, sensor, device, or enhanced or unenhanced human eye from differentiating a labeled composition from an unlabeled composition. Examples of labels include, but are not limited to: a radioactive isotope or chelate thereof, dye (fluorescent or nonfluorescent) stain, enzyme, or nonradioactive metal. Specific examples include, but are not limited to: fluorescein, biotin, digoxigenin, alkaline phosphatase, biotin, streptavidin, $^{3}H$, $^{14}C$, $^{32}P$, $^{35}S$, or any other compound capable of emitting radiation, rhodamine, 4-(4'-dimethylamino-phenylazo)benzoic acid (“Dabcyl”); 4-(4'-dimethylamino-phenylazo)sulfonic acid (sulfonyl chloride) (“Dabsyl”); 5-((2-aminoethyl)-amino)-naphtalene-1-sulfonic acid (“EDANS”); Psoralene derivatives, haptens, cyanines, acridines, fluorescent rhodol derivatives, cholesterol derivatives; ethylenediaminetetraaceticacid (“EDTA”) and derivatives thereof, or any other compound that may be differentially detected. The label may also include one or more fluorescent dyes optimized for use in genotyping. Examples of such dyes include, but are not limited to: dR110, 5-FAM, 6FAM, dR6G, JOE, HEX, VIC, TET, dTAMRA, TAMRA, NED, dROX, PET, BHQ+, Gold540, and LIZ. In one embodiment, the probe comprising SEQ ID NO: 2 is labeled with 6FAM at 5' end and MGB-NFQ at 3' end.

Methods of detecting the presence of a gene or an allele further include, but are not limited to, any form of DNA sequencing including Sanger, next generation sequencing, pyrosequencing, sequencing by ligation, sequencing by synthesis, single molecule sequencing, pooled, and barcoded DNA sequencing or any other sequencing method now known or yet to be disclosed; or any other method that allows the detection of a particular nucleic acid sequence within a sample or enables the differentiation of one nucleic acid from another nucleic acid that differs from the first nucleic acid by one or more nucleotides, or any combination of these.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP) are added to each of four reactions (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a phyrophosphate upon nucleotide incorporation. An ATP sulfurylase enzyme converts pyrophosphate into ATP which, in turn, catalyzes the conversion of luciferin to oxyluciferin which results in the generation of visible light that is then detected by a camera.

In sequencing by ligation, such as, SOLID™ sequencing, the molecule to be sequenced is fragmented and used to prepare a population of clonal magnetic beads, in which each bead is conjugated to a plurality of copies of a single fragment with an adaptor sequence, and alternatively, a barcode sequence. The beads are bound to a glass surface. Sequencing is then performed through 2-base encoding.

In sequencing by synthesis, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

III Kits.

Kits that facilitate methods of detecting a strain or species specific sequence may include one or more of the following reagents: specific nucleic acids such as oligonucleotides, labeling reagents, enzymes including PCR amplification reagents such as the thermostable DNA polymerases Taq or Pfu, reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the technology, the specific nucleic acid comprises one or more oligonucleotides capable of hybridizing to the marker.

A kit may also contain an indication that links the output of the kit to a particular result. For example, an indication may be one or more sequences or that signify the identification of a particular fungal phylum, class, order, family, genus species, subspecies, strain or any other delineation of a group of fungi. An indication may include a Ct value, wherein exceeding the Ct value indicates the presence or absence of an organism of interest. A kit may contain a positive control. A kit may contain a standard curve configured to quantify the amount of fungus present in a sample. An indication includes any guide that links the output of the kit to a particular result. The indication may be a level of fluorescence or radioactive decay, a value derived from a standard curve, or from a control, or any combination of these and other outputs. The indication may be printed on a writing that may be included in the kit or it may be posted on the Internet or embedded in a software package.

EXAMPLES

Various embodiments of the present teachings can be illustrated by the following non-limiting examples. The following embodiments and examples are illustrative, and are not intended to limit the scope of the claims.

Example 1—Method and Material—CocciDxQ

The assay employs TaqMan MGB-6FAM fluorescent probe and a multiplex set of three forward primers and 4 reverse primers (Table 1 above). The assay reactions can be performed using Real Time PCR Mastermix of choice, but has been optimized for use with Quanta Biosciences PerfeCTa® qPCR FastMix®, UNG, ROX™. Thermocycling conditions consist of UNG activation for 3 min at 50° C. followed by 10 min Taq Polymerase activation at 95° C. and 50 PCR cycles of 15 s at 95° C. and 1 min at 60° C. Each reaction produced an amplification plot yielding a cycle-threshold (Ct) value directly proportional to the initial concentration of DNA in the reaction.

Example 2—Sensitivity and Specificity of the Cocci Quantitative Diagnosis Assay—CocciDxQ (1) Determining Limit of Detection The Limit of Detection (LOD), also called the Detection Limit or Lower Limit of Detection, is the lowest quantity of a substance that can be distinguished from the absence of that substance (i.e., a blank value) within a stated confidence limit. LOD is hereby used to describe the sensitivity of quantitative assays. The assay target region, a multi-copy target having the advantage of being detected at low levels in comparison to a single-copy target was utilized in the LOD test. Although the copy number of assay target region in *Coccidioides* isolates, including *C. immitis* and *C. posadasii*, varies, however, the average number of target copies in a *Coccidioides* genome is estimated at 85. Therefore, the ability of an assay in detecting the target region provides a method for relative quantification of *Coccidioides* fungal load.

The analytical LOD of the CocciDxQ assay is 15 target copies/ul (Table 3). This translates to less than one genome/ul. Genomic DNA was quantified and limiting serial dilutions were created to test the LOD. Dilutions were queried across the CocciDxQ assay with 20 replicates each. Finally, to establish the LOD, dilutions for which at least 19 of 20 replicates amplified were further evaluated by testing 64 replicates and exhibited at least 95% amplification (61/64 amplification ratio). Results are shown in Table 3.

TABLE 3

Determination of Limit of Detection of CocciDxQ assay:

| Dilution of Target Copies/ 1 ul | Amplification Ratio of 20 Replicate Screen | Amplification Ratio of 64 Replicate Screen | Mean Ct | CocciDxQ Limit of Detection (Target Copies/ 1 ul) |
|---|---|---|---|---|
| 25 | 20/20 | 62/64 | 31.08 | 15 copies/ 1 µl (Ct = 31.72, Ct std. dev. = 0.77) |
| 15 | 20/20 | 62/64 | 31.72 | |
| 10 | 19/20 | 58/64 | 32.61 | |
| 5 | 17/20 | N/A | 36.93 | |
| 3 | 14/20 | N/A | 37.74 | |
| 1 | 6/20 | N/A | 37.80 | |
| 0.1 | 2/20 | N/A | 36.45 | |
| 0.01 | 3/20 | N/A | 38.08 | |

The analytical limit of detection of the assay is 15 target copies/ul, that means if the copy number/1 µl of the genomic target in a sample is lower than 15, the CocciDxQ assay may not be sensitive enough to either reliably detect the presence or absence of the target, nor a reliable calculation of the copy number of a target DNA in the sample. However, the sensitivity of the CocciDxQ assay is imparted by high genomic copy number of the target region, an area associated with a copia-like retrotransposon, which is 85 copies/genome. That is to say that the CocciDxQ assay as disclosed herein can detect equivalent to less than one genomic DNA molecule per microliter of DNA, which is highly sensitive.

(2) Assay Specificity

To further illustrate the specificity of the CocciDxQ assay, the assay was tested against a panel of 89 diagnostic differential DNA's including differential diagnostic isolates and near neighbor or background isolates to detect any cross reactivity. All assay results were negative (see Table 4), indicating the sample species does not contain *C. immitis* and *C. posadasii* specific sequence amplifiable using the CocciDxQ assay comprising probe and primer sets in Table 1, and thus proved the assay specificity.

TABLE 4

List of DNA that the CocciDxQ Assay was screened across.

| | |
|---|---|
| Human gDNA | *Streptococcus pneumoniae* |
| *Burkholderia pseudomallei* | *Staphylococcus capitis* |
| *Streptococcus lactis* | *Mycoplasma pneumoniae* |
| *Streptococcus oralis* | *Enterobacter cloacae* |
| *Haemophilus Influenzae* | *Streptococcus mitis* |
| *Acinetobacter baumanni* | *Streptococcus salivarius* |
| *Streptococcus thermophilus* | Methicillin Resistant *Staphylococcus aureus* |
| *Streptococcus anginosus* | Methicillin Sensitive *Staphylococcus aureus* |
| *Streptococcus mutans* | *Micrococcus* sp |
| *Staphylococcus arlettae* | *Chryseobacterium indologenes* |
| *Staphylococcus chonii* | *Klebsiella oxytoca* |
| *Staphylococcus equorum* | *Enterococcus faecalis* |
| *Staphylococcus gallinarum* | *Haemophilus parainfluenzae* |
| *Staphylococcus hominis* | *Achromobacter xylosoxidans* |
| *Staphylococcus kloosii* | *Staphylococcus xylosus* |
| *Staphylococcus lugdunensis* | *Klebsiella pneumoniae* |
| *Streptococcus gordonii* | *Moraxella catarrhalis* |
| *Streptococcus equi* | *Staphylococcus epidermidis* |
| *Streptococcus uberis* | *Staphylococcus haemolyticus* |
| *Providencia stuartii* | *Streptococcus pyogenes* |

TABLE 4-continued

List of DNA that the CocciDxQ Assay was screened across.

| | |
|---|---|
| *Corynebacterium jeikeium* | *Acremonium strictum* |
| *Stenotrophomonas maltophilia* | *Bacillus anthracis* |
| *Fusobacterium nucleatum* | *Brucella abortus* |
| *Corynebacterium diphtheriae* | *Candida famata* |
| *Porphyromonas gingivalis* | *Candida haemulonii* |
| *Cryptococcus neoformans* | *Candida lusitaniae* |
| *Mycobacterium avium* | *Chaetomium globosum* |
| *Aspergillus niger* | *Eschericha coli* |
| *Penicillium marneffei* | *Francisella tularensis* |
| *Eikenella corrodens* | *Fusarium solani* |
| *Enterobacter aerogenes* | *Geotrichum candidum* |
| *Staphylococcus saprophyticus* | *Histoplasma capsulatum* |
| *Pseudomonas aeruginosa* | *Legionella pneumophila* |
| *Neisseria meningitidis* | *Listeria monocytogenes* |
| *Entercoccus faecium* | *Paecilomyces variotii* |
| *Neisseria gonorrhoeae* | *Pichia ohmeri* |
| *Burkholderia cepacia* | *Rhizopus oryzae* |
| *Bordetella bronchiseptica* | *Salmonella typhimurium* |
| *Candida albicans* | *Sporothrix schenckii* |
| *Bacteroides fragilis* | *Trichosporon asteroides* |
| *Bacteroides uniformis* | *Trichosporon faecale* |
| *Streptococcus agalactiae* | *Trichosporon ovoides* |
| *Candida glabrata* | *Uncinocarpus reesi* |
| *Candida parapsilosis* | *Burkholderia ubonensis* |
| *Candida tropicalis* | |

The CocciDxQ assay was further screened across samples containing *Coccidioides* spp. using DNA extracts or whole genome amplifications of DNA extracts, and the assay detected *Coccidioides* spp. in 559 out of a total number of 560 samples.

Example 3—CocciDxQ Assay for Clinical Specimen

Clinical specimen suspected having *Coccidioides* spp. were tested with the CocciDxQ assay. DNA was extracted from specimens which were blood, sputum, saliva, urine, or sputum-LSA. The test results provided in Table 5 show that sputum samples provide template (e.g., DNA) suitable for the CocciDxQ assay.

TABLE 5

CocciDxQ test using DNA of clinical samples

| Specimen Type | Amplification rate (# of samples tested) | Mean Ct |
|---|---|---|
| Blood | 0 (13) | n/a |
| Sputum | 1 (6) | 37.2 |
| Saliva | 0 (14) | n/a |
| Urine | 0 (13) | n/a |
| Sputum-LSA | 16 (25) | 27.5 |

DNA and RNA extracted from pleural fluid specimens were also tested using the CocciDxQ assay. The Real-Time PCR results are shown in Table 6.

TABLE 6

CocciDxQ assay for clinical pleural fluid specimens

| Sample | CocciDxQ Ct on DNA | CocciDxQ Ct on RNA |
|---|---|---|
| 3838H | Neg | 38.0 |
| 0681J | Neg | 37.1 |
| 8056G | Neg | Neg |
| 7477G | Neg | Neg |

TABLE 6-continued

| CocciDxQ assay for clinical pleural fluid specimens | | |
|---|---|---|
| Sample | CocciDxQ Ct on DNA | CocciDxQ Ct on RNA |
| 9294H | 35.1 | 37.6 |
| 9496G | Neg | Neg |
| 5308G | Neg | Neg |

Neg = negative for target

The results from Table 6 illustrate that RNA can also be used as an assay target/template, in addition to DNA, if a reverse transcription step is used to generate cDNA. Further, *Coccidioides* was detected in several samples that had negative detection results in DNA. Thus, these results could demonstrate that RNA detection of *Coccidioides* can be used in addition to, or in place of DNA-based detection of *Coccidioides*.

Another set of clinical specimen were tested with the CocciDxQ assay using both DNA and RNA from each specimen, and the results are provided in Table 7:

TABLE 7

| CocciDxQ assay for clinical specimen | | | | | | | | | | |
|---|---|---|---|---|---|---|---|---|---|---|
| | DNA | | | | | RNA | | | | |
| | | Comparison real-time assays to ITS | | Control real-time PCR | | | | Comparison real-time assays to ITS | Comparison real-time assays to ITS | |
| Sample Name | CDxQ | CQ34 | CQBD | 16S | ALU | CDxQ | CQ34 | CQBD | 16S | ALU |
| TG004-2_saliva | Neg | Neg | Neg | 30.7 | NR | Neg | Neg | Neg | 21.0 | 25.4 |
| TG006_saliva | Neg | Neg | Neg | 31.5 | 19.6 | Neg | Neg | Neg | 26.2 | 22.3 |
| TG006-2_saliva | Neg | Neg | Neg | 28.7 | 20.7 | Neg | Neg | Neg | 25.9 | 23.7 |
| TG009_saliva | Neg | Neg | Neg | 29.9 | 17.6 | Neg | Neg | Neg | 22.2 | 20.0 |
| TG009-2_saliva | Neg | Neg | Neg | 26.1 | 20.5 | Neg | 38.6 | Neg | 24.4 | 7.3 |
| TG010_saliva | Neg | Neg | Neg | 31.3 | 21.0 | Neg | Neg | Neg | 23.7 | 20.1 |
| TG010-2_saliva | Neg | Neg | Neg | 32.1 | 21.0 | Neg | Neg | Neg | 27.1 | 18.8 |
| TG010-2_sputum | Neg | Neg | Neg | 32.1 | NR | Neg | Neg | Neg | 31.6 | 16.1 |
| TG011_sputum | Neg | Neg | Neg | 24.4 | NR | Neg | Neg | Neg | 25.0 | 18.4 |
| TG012_saliva | Neg | Neg | Neg | 31.7 | 21.6 | Neg | Neg | Neg | 29.2 | 24.7 |
| TG012-2_saliva | Neg | Neg | Neg | 31.8 | 17.3 | Neg | Neg | Neg | 28.7 | 19.6 |
| TG012-2_sputum | Neg | Neg | Neg | 28.7 | NR | Neg | Neg | Neg | Neg | 31.7 |
| TG012-3_saliva | Neg | Neg | Neg | 31.8 | 20.3 | Neg | Neg | Neg | 27.6 | 21.2 |
| TG013_sputum | 38.2 | 37.7 | Neg | 30.8 | 26.4 | 27.8 | 25.3 | Neg | 28.3 | 19.0 |
| TG013_saliva | Neg | Neg | Neg | 24.4 | NR | Neg | Neg | Neg | 24.8 | 19.0 |
| TG013_sputum | Neg | Neg | Neg | 24.4 | NR | 36.9 | 35.1 | Neg | 16.2 | 12.9 |
| TG014_saliva | Neg | Neg | Neg | 31.9 | NR | Neg | Neg | Neg | 27.9 | 34.4 |
| TG015_saliva | Neg | Neg | Neg | 30.8 | 21.0 | Neg | Neg | Neg | 25.3 | 21.6 |
| TG015-2_sputum | Neg | Neg | Neg | 23.7 | NR | Neg | Neg | Neg | 21.5 | 24.8 |
| TG016_sputum | Neg | Neg | Neg | 21.6 | NR | Neg | Neg | Neg | 16.4 | 12.8 |
| PC (DNA only) | 17.3 | 20.9 | 20.4 | 9.9 | NR | NR | NR | NR | NR | NR |

Example 4—CocciENV

With the discovery of new alleles of SEQ ID NO: 1 (i.e., the target sequence of CocciDxQ and CocciENV), additional oligonucleotides (SEQ ID NOs: 10-38) were generated to bind to and amplify some or all of the known alleles of SEQ ID NO: 1. In brief, Ccpy numbers of the target sequence (SEQ ID NO: 1) in *Coccidioides* genomes were estimated bioinformatically using whole genome sequence with this updated information. Using the Taqman probe sequence (SEQ ID NO: 2), each genome was queried via BLAST for hits with 100% identity and 100% coverage. For each hit, the probe and flanking sequence were extracted and aligned to confirm the region's homology to the assay target (SEQ ID NO: 1).

The CocciENV assay is configured to be run as a real-time PCR reaction using substantially similar conditions as recited above for the CocciDxQ assay, but with modifications as to the oligonucleotide content. In short, the CocciENV assay uses the same probe (SEQ ID NO: 2), but replaces the CocciDxQ forward and reverse primers (SEQ ID NOs: 3-9) with the forward and reverse primers detailed in Table 2 (SEQ ID NOs: 10-38).

The CocciEnv assay was subject to concise validation, given the extensive validation of CocciDxQ (described above), but included sensitivity and specificity screening across a subset of the target molecules mentioned above, and added DNA from four additional Onygenales species that are more phylogenetically closely related to *Coccidioides* spp: *Amauroascus mutatus, A. niger, Byssoonygena ceratinophila*, and *Chrysosporium queenslandicum.*

Example 5—CocciENV Development and Validation

A. Methods

With the recent database deposition of new *Coccidioides* genome sequences, we hypothesized that more variant alleles of the CocciDxQ target would be available, and that we could add primers to the original assay to capture more variants of the target, thus increasing the sensitivity of the assay. Using a local BLAST database of all available *Coccidioides* genomes and the CocciDxQ Taqman probe sequence as a query, each genome was queried for hits with 100% identity and 100% coverage. For each hit, the probe and flanking sequence were extracted using an in-house script and aligned to confirm the region's identity to the assay target. We designed several new primers to increase the number of alleles of the target captured by the assay, and refer to the enhanced assay as CocciEnv. The new assay was run using the same conditions as for CocciDxQ, with only primer concentrations modified (Table 8).

TABLE 8

| Assay component | Sequence | SEQ ID NO: | Final concentration in PCR (uM) |
|---|---|---|---|
| CDx_F1d1 | CGTTGCACRGGGAGCACCT | 10 | 0.375 |
| CDx_F2 | AAGCTTTGGATCTTTGTGGCTCT | 11 | 0.375 |
| CDx_F3 | AATTGATCCATTGCAAGCACCT | 12 | 0.25 |
| CDx_F4 | AATCCAACCTTTGGAACTACACCT | 13 | 0.25 |
| CDx_F5 | TTTTCCGGTATGGACTAGCACCT | 14 | 0.375 |
| CDx_F6d2 | TGTTAGGTAATCYAACYAGCACCT | 15 | 0.125 |
| CDx_F7d2 | TRTTAGGTAATYCAACTAGCACCT | 16 | 0.125 |
| CDx_F8d1 | TGTTAGATAATCCAACYAGCACCT | 17 | 0.125 |
| CDx_F9d2 | GKTARGTAATCCAACTAGCACCT | 18 | 0.125 |
| CDx_F10d2 | TGTTAGGTARTCCAACTAGCAYCT | 19 | 0.125 |
| CDx_F11d2 | TGTTAGGTAATCCAACTMGCACYT | 20 | 0.125 |
| CDx_R1 | GATGGAGGACTCTATATGCTTGT | 21 | 0.375 |
| CDx_R2 | ATGGAGGACTCGTTATGCCTGT | 22 | 0.375 |
| CDx_R3 | GGAGGACCCGTATGCTTGTGT | 23 | 0.375 |
| CDx_R4 | TGCTAAATGATGGAGGGCTTGT | 24 | 0.375 |
| CDx_R5 | GATGGAGGCTCGTATGCTTGT | 25 | 0.375 |
| CDx_R6 | AAGGGGTTTGTGGTGAATCCTTA | 26 | 0.375 |
| CDx_R7 | CAGAAAAATAGCCGTATGCTTGT | 27 | 0.375 |
| CDx_R8d2 | TRATGGAGRACTTGTATGCTTGT | 28 | 0.125 |
| CDx_R9d1 | TGATGGAGGACTCGTATGCYTGT | 29 | 0.125 |
| CDx_R10d2 | TGATGGARRACTCATATGCTTGT | 30 | 0.125 |
| CDx_R11d2 | TGATAGAGAACTTGTATRCTTRT | 31 | 0.125 |
| CDx_R12d2 | TGATGAAGAACTTRTATRCTTGT | 32 | 0.125 |
| CDx_R13d2 | TGATRRAGGACTTGTATGCTTGT | 33 | 0.125 |
| CDx_R14 | TGATGGAAAACTTGTATGCTTGT | 34 | 0.125 |
| CDx_R15d2 | TGATGGAGGACTTGTAYAYTTGT | 35 | 0.125 |
| CDx_R16d2 | TGATGGAGGACTTGTAYGCTTRT | 36 | 0.125 |
| CDx_R17d2 | TGATGGAGGACTYATATGCTTRT | 37 | 0.125 |
| CDx_R18d2 | GATGGAGGACTCGTWYGCTTGT | 38 | 0.125 |
| CDx_FMGB | 6FAM-ACCCACATAGATTAGC-MGBNFQ | 2 | 0.25 |

CocciEnv was subject to a more concise validation than described above, given the extensive validation of CocciDxQ, but included sensitivity and specificity screening across a subset of the DNAs used for CocciDxQ validation (n=94 *Coccidioides* WGA DNAs, n=89 non-target DNAs Table 9), along with DNA from four additional Onygenales species: *Amauroascus mutatus* ATCC® 90275, *A. niger* ATCC® 22339, *Byssoonygena ceratinophila* ATCC® 64724, and *Chrysosporium queenslandicum* ATCC® 4404. Additionally, CocciDxQ and CocciEnv were compared side-by-side by screening DNAs from 23 *Coccidioides* isolates.

B. Results

The CocciDxQ assay was positive on the whole-genome-amplified DNA of all 556 unique isolates of *Coccidioides* (Table 10), and was negative on all DNA from various species (Table 9) including the four Onygenales family members, illustrating 100% sensitivity and 100% specificity. The abbreviated validation showed that CocciEnv also demonstrated 100% sensitivity and specificity.

TABLE 9

Isolate gDNAs screened to confirm specificity of CocciDxQ and CocciEnv assays.

| Species ID | Strain ID |
|---|---|
| Human | |
| *Streptococcus lactis* | 22c |
| *Streptococcus oralis* | 22d |
| *Haemophilus Influenzae* | PU5-052 |
| *Acinetobacter baumanni* | ACBA-3 |
| *Streptococcus thermophilus* | BAA-250 |
| *Streptococcus anginosus* | 33397 |
| *Streptococcus mutans* | 700610 |
| *Staphylococcus arlettae* | 43957 |
| *Staphylococcus chonii* | 29974 |
| *Staphylococcus equorum* | 43958 |
| *Staphylococcus gallinarum* | 35539 |
| *Staphylococcus hominis* | 27844 |
| *Staphylococcus kloosii* | 43959 |
| *Staphylococcus lugdunensis* | 43809 |
| *Streptococcus gordonii* | 10558 |
| *Streptococcus equi* | 9528 |
| *Streptococcus uberis* | 700407 |
| *Providencia stuartii* | PROV-1 |
| *Corynebacterium jeikeium* jk grp | COJE-1 |
| *Stenotrophomonas maltophilia* | STMA-10 |
| *Fusobacterium nucleatum* | ATCC25586D-5 |
| *Corynebacterium diphtheriae* | ATCC700971D-5 |
| *Porphyromonas gingivalis* | ATCC33277D-5 |
| *Cryptococcus neoformans* | ATCC208821D-2 |
| *Mycobacterium avium* | BAA-968D-5 |
| *Aspergillus niger* | 1015D-2 |
| *Penicillium marneffei* | 18224-D2 |
| *Eikenella corrodens* | 51724D |
| *Enterobacter aerogenes* | 15038D-5 |
| *Pseudomonas aeruginosa* | PSAR-64 |
| *Neisseria meningitidis* | CRS8-001 |
| *Entercoccus faecium* | VRE-33 |
| *Neisseria gonorrhoeae* | CRS6-374 |
| *Burkholderia cepacia* | ATCC 25608 |
| *Bordetella bronchiseptica* | ATCC 10580 |
| *Candida albicans* | ATCC 14053 |
| *Bacteroides fragilis* | ATCC 25285 |
| *Bacteroides uniformis* | ATCC 8492 |
| *Streptococcus agalactiae* | CRS4-147 |
| *Candida glabrata* | YT-48 |
| *Candida parapsilosis* | YT-49 |
| *Candida tropicalis* | YT-50 |
| *Streptococcus pneumoniae* | STPN-187 |
| *Staphylococcus capitis* | CNS-125 |
| *Mycoplasma pneumoniae* | 15531 |
| *Enterobacter cloacae* | CRS4-429 |

TABLE 9-continued

Isolate gDNAs screened to confirm specificity of CocciDxQ and CocciEnv assays.

| Species ID | Strain ID |
|---|---|
| *Streptococcus mitis* | STMI-1 |
| *Streptococcus salivarius* | SSAL-1 |
| Methicillin Resistant *Staphylococcus aureus* | MRSA-653 |
| Methicillin Sensitive *Staphylococcus aureus* | MSSA-309 |
| *Micrococcus* sp | MIC-3 |
| *Chryseobacterium indologenes* | CHIN-8 |
| *Klebsiella oxytoca* | KOXY-142 |
| *Enterococcus faecalis* | EFA-115 |
| *Haemophilus parainfluenzae* | HPAR-304 |
| *Achromobacter xylosoxidans* | ACXY-2 |
| *Staphylococcus xylosus* | ATCC-35033 |
| *Klebsiella pneumoniae* | SP-1237, KLPN-143 |
| *Moraxella catarrhalis* | MCAT-108 |
| *Staphylococcus epidermidis* | HIP04645 |
| *Staphylococcus haemolyticus* | N/A |
| *Streptococcus pyogenes* | GAS-143 |
| *Coccidioides posadasii* | 3224 |
| *Coccidioides posadasii* | 3231 |
| *Acremonium strictum* | |
| *Candida famata* | |
| *Candida haemulonii* | |
| *Candida lusitaniae* | |
| *Chaetomium globosum* | |
| *Coccidioides immitis* | |
| *Eschericha coli* 0157:H7 | ATCC35150 |
| *Francisella tularensis* | LVS |
| *Fusarium solani* | |
| *Geotrichum candidum* | |
| *Histoplasma capsulatum* | |
| *Legionella pneumophila* | ATCC 33152 |
| *Listeria monocytogenes* | H2446 |
| *Paecilomyces variotii* | |
| *Pichia ohmeri* | |
| *Rhizopus oryzae* | |
| *Salmonella typhimurium* | LT1 |
| *Sporothrix schenckii* | |
| *Trichosporon asteroides* | |
| *Trichosporon faecale* | |
| *Trichosporon ovoides* | |
| *Uncinocarpus reesi* | |
| *Yersinia pestis* | FV-1 |
| *Burkholderia ubonensis* | NCTC13147 |
| *Amauroascus mutatus* | |
| *Amauroascus niger* | |
| *Byssoonygena ceratinophila* | |
| *Chrysosporium queenslandicum* | |

TABLE 10

Isolate gDNA (whole genome amplified) screened with CocciDxQ assay. A subset of these samples (n = 94) was screened with CocciEnv assay. For origin, C = clinical and E = environmental.

| TGC ID# | Species ID | Strain ID | RMSCC#/Alternate ID | Isolation/Disease Information Source | Origin |
|---|---|---|---|---|---|
| TGC0001 | *C. posadasii* | 8178 | ID05- 2440008178, KJK004 | Bronchial wash | C |
| TGC0002 | *C. posadasii* | 8533 | ID05- 2560008533, KJC010 | Bronchial wash | C |
| TGC0003 | *C. posadasii* | 8589 | ID05- 2570008589, KJB010 | Tissue, left cheek | C |
| TGC0004 | *C. posadasii* | 63029 | | bronch wash | |
| TGC0005 | *C. posadasii* | 8700 | ID05- 2620008700, KJA011 | Ankle tissue | C |
| TGC0006 | *C. posadasii* | 8835 | ID05- 2650008835, KJA012e | Bronchial wash | C |
| TGC0008 | *C. posadasii* | 63394 | | R. lung wash | |
| TGC0009 | *C. posadasii* | 8885 | ID05- 2690008885, KJK008f | Blood | C |
| TGC0010 | *C. posadasii* | 8860 | | Unknown | |
| TGC0011 | *C. posadasii* | 8973 | ID05- 2700008973, KJA014g | Bone marrow | C |
| TGC0012 | *C. posadasii* | 9001 | ID05- 2710009001, KJB011 | Sputum | C |
| TGC0013 | *C. posadasii* | 9120 | ID05-2760009120 | Blood | C |
| TGC0015 | *C. posadasii* | 63363 | | bronch wash | |
| TGC0016 | *C. posadasii* | 63360 | | bronch wash | |
| TGC0017 | *C. posadasii* | 63078 | | wash/aspirate | |
| TGC0018 | *C. posadasii* | 10512 | | bronch wash | |

TABLE 10-continued

Isolate gDNA (whole genome amplified) screened with CocciDxQ assay. A subset of these samples (n = 94) was screened with CocciEnv assay. For origin, C = clinical and E = environmental.

| TGC ID# | Species ID | Strain ID | RMSCC#/Alternate ID | Isolation/Disease Information Source | Origin |
|---|---|---|---|---|---|
| TGC0019 | *C. posadasii* | 10569 | | sputum | |
| TGC0020 | *C. posadasii* | 10816 | | CSF | |
| TGC0021 | *C. posadasii* | 10995 | | bronch wash | |
| TGC0022 | *C. posadasii* | 10997 | | sputum | |
| TGC0023 | *C. posadasii* | 11166 | | LUL BAL | |
| TGC0024 | *C. posadasii* | 11206 | | tissue | |
| TGC0025 | *C. posadasii* | 969 | ID05- 0340000969, KJE001 | Bronchial wash | C |
| TGC0026 | *C. posadasii* | 152 | | aspirate | |
| TGC0027 | *C. posadasii* | 150 | | sputum | |
| TGC0028 | Unknown | 151 | | swab | |
| TGC0029 | *C. posadasii* | 3718 | | RML wash | |
| TGC0030 | *C. posadasii* | 3601 | | BAL RLL | |
| TGC0031 | *C. posadasii* | 94 | | body fluid | |
| TGC0032 | *C. immitis* | 3698 | RMSCC 3698 | ~ | ~ |
| TGC0033 | *C. posadasii* | 15 | | sputum | |
| TGC0034 | *C. posadasii* | 11224 | | sputum | |
| TGC0035 | *C. posadasii* | 11226 | | sputum | |
| TGC0036 | *C. posadasii* | 11223 | | bronch wash | |
| TGC0037 | *C. posadasii* | 3632 | | right lung nodule | |
| TGC0038 | *C. posadasii* | 416 | ID05- 0180000416, KJD001 | Bronchial wash | C |
| TGC0039 | *C. posadasii* | 678 | ID05- 0250000678, KJC002 | Bronchial wash | C |
| TGC0040 | *C. posadasii* | 295 | ID05- 0120000295, KJC001 | Elbow fluid | C |
| TGC0041 | *C. posadasii* | 3621 | | sputum | |
| TGC0042 | *C. posadasii* | 276 | ID05-0110000276 | Knee fluid | C |
| TGC0043 | *C. posadasii* | 153 | | tissue | |
| TGC0044 | *C. posadasii* | 2928 | ID05- 0750002928, KJA003 | Bronchial wash | C |
| TGC0045 | *C. posadasii* | 3402 | ID05- 08200003402, KJF002 | Elbow tissue | C |
| TGC0046 | Unknown | 1628 | | sputum | |
| TGC0047 | *C. posadasii* | 2870 | ID05- 0740002870, KJA002 | Bronchial wash | C |
| TGC0048 | *C. posadasii* | 1246 | ID05- 0420001246, KJC003 | Bronchial wash | C |
| TGC0049 | *C. posadasii* | 10996 | | bronch wash | |
| TGC0050 | *C. posadasii* | 62461 | | Leukens Trap (?) | |
| TGC0051 | *C. posadasii* | 93 | | Unknown | |
| TGC0052 | *C. posadasii* | 61107 | | wash/aspirate | |
| TGC0053 | *C. posadasii* | 61833 | | Unknown | |
| TGC0054 | *C. posadasii* | 5521 | | BAL RLL | |
| TGC0055 | *C. posadasii* | 06-920 | | RLLL tissue | |
| TGC0056 | *C. posadasii* | 11492 | | neck mass | |
| TGC0057 | *C. posadasii* | 5804 | ID05- 1650005804, KJA008 | Bronchial wash | C |
| TGC0058 | *C. posadasii* | 62248 | | RUL wash | |
| TGC0059 | Unknown | 3761 | | bronch wash | |
| TGC0060 | *C. posadasii* | 06-1110 | | unknown | |
| TGC0061 | *C. posadasii* | 4171 | ID05- 1100004171, KJB004 | Bronchial wash | C |
| TGC0062 | *C. posadasii* | 61961 | | sacral mass | |
| TGC0063 | *C. posadasii* | 62165 | | lung tissue | |
| TGC0064 | *C. posadasii* | 4916 | ID05- 13300004916, KJE002b | Bronchial wash | C |
| TGC0065 | Unknown | 2219 | | CSF | |
| TGC0066 | *C. posadasii* | 2454 | | L arm node | |
| TGC0067 | *C. posadasii* | 3399 | | paratracheal node | |
| TGC0068 | *C. posadasii* | 3359 | f0702 | Pleural fluid | C |
| TGC0069 | Unknown | 61312 | | CSF | |
| TGC0070 | *C. posadasii* | 62962 | | bronch RML | |
| TGC0071 | *C. posadasii* | 62987 | | bronch wash | |
| TGC0072 | *C. posadasii* | 62868 | | bronch wash | |
| TGC0073 | *C. posadasii* | 61948 | | bronch wash | |
| TGC0074 | *C. posadasii* | 62882 | | lung fluid | |
| TGC0075 | *C. posadasii* | 11414 | | bronch wash | |
| TGC0076 | *C. posadasii* | 61109 | | unknown swab | |
| TGC0077 | *C. posadasii* | 61855 | | lung-right | |
| TGC0078 | *C. posadasii* | 61812 | | BAL | |
| TGC0079 | *C. posadasii* | 61859 | | bronch wash | |
| TGC0080 | *C. posadasii* | 61414 | | unknown | |
| TGC0081 | *C. posadasii* | 5523 | ID05- 1540005523, KJB007c | Bronchial wash | C |
| TGC0082 | *C. posadasii* | 5579 | ID05- 1570005579, KJA007 | Bronchial wash | C |
| TGC0083 | *C. posadasii* | 6961 | | bronch wash | |
| TGC0084 | *C. posadasii* | 6840 | | BAL | |
| TGC0085 | *C. posadasii* | 62215 | | bronch wash | |
| TGC0086 | *C. posadasii* | 62628 | | bronch wash | |
| TGC0087 | *C. posadasii* | 1024 | ID05- 0380001024, KJF001 | Knee Fluid | C |
| TGC0088 | *C. posadasii* | 3453 | | Trans trachea | C |
| TGC0089 | *C. posadasii* | 1130 | ID05- 0400001130, KJD002 | Knee Fluid | C |
| TGC0090 | *C. posadasii* | 1298 | ID05- 04200001298, KJB003 | Bronchial wash | C |
| TGC0091 | *C. posadasii* | 3833 | ID05-0970003833, KJA004 | Bronchial wash | C |

TABLE 10-continued

Isolate gDNA (whole genome amplified) screened with CocciDxQ assay. A subset of these samples (n = 94) was screened with CocciEnv assay. For origin, C = clinical and E = environmental.

| TGC ID# | Species ID | Strain ID | RMSCC#/Alternate ID | Isolation/Disease Information Source | Origin |
|---|---|---|---|---|---|
| TGC0092 | *C. posadasii* | 3614 | ID05- 0890003614, KJC004 | Lung Tissue | C |
| TGC0093 | *C. posadasii* | 4000 | ID05-1030004000, KJC005 | Lung Tissue | C |
| TGC0094 | *C. posadasii* | 3656 | | lung tissue | |
| TGC0095 | *C. posadasii* | 4038 | ID05- 10500004038, KJD003 | Chin Abscess | C |
| TGC0096 | *C. posadasii* | 7835 | ID05- 2310007835, KJA010 | Bronchial wash | C |
| TGC0097 | *C. posadasii* | 4273 | ID05- 1150004273, KJC006 | Lung Tissue | C |
| TGC0098 | *C. posadasii* | 4581 | ID05- 1240004581, KJB005c | Bronchial wash | C |
| TGC0099 | *C. posadasii* | 4644 | ID05- 1260004644, KJK002a | Systemic; urogenital | C |
| TGC0100 | *C. posadasii* | 4645 | | body fluid | |
| TGC0102 | *C. posadasii* | 4947 | ID05-1360004947, KJA005 | Sputum | C |
| TGC0103 | *C. posadasii* | 4948 | ID05-1360004948, KJA006 | Human | C |
| TGC0104 | *C. posadasii* | 5003 | ID05- 1370005003, KJM002 | Sputum | C |
| TGC0105 | *C. posadasii* | 5032 | ID05-1380005032 | Human | C |
| TGC0106 | *C. posadasii* | 5354 | ID05- 1470005354, KJF003 | Sputum | C |
| TGC0107 | Unknown | 11227 | | bronch wash | |
| TGC0108 | *C. posadasii* | 11276 | | scalp mass | |
| TGC0109 | *C. posadasii* | 11309 | | bronch wash | |
| TGC0110 | Unknown | 11311 | | bronch wash | |
| TGC0111 | *C. posadasii* | 11318 | | sputum | |
| TGC0112 | *C. posadasii* | 11337 | | thorocentesis | |
| TGC0113 | *C. posadasii* | 11436 | | RUL fluid | |
| TGC0114 | *C. posadasii* | 11461 | | bronch wash | |
| TGC0115 | *C. posadasii* | 11467 | | leukens trap (?) | |
| TGC0116 | *C. posadasii* | 11482 | | sputum | |
| TGC0117 | Unknown | 11524 | | BAL | |
| TGC0118 | *C. posadasii* | 11491 | | back wound | |
| TGC0119 | *C. posadasii* | 11610 | | bronch wash | |
| TGC0120 | *C. posadasii* | 11615 | | sputum | |
| TGC0121 | *C. posadasii* | 11625 | | BAL RML | |
| TGC0122 | *C. posadasii* | 11676 | | lymph node | |
| TGC0123 | *C. posadasii* | 11723 | | bronch wash | |
| TGC0124 | *C. posadasii* | B16 | BT05- 0810000016, KJG002 | Pulmonary | C |
| TGC0125 | *C. posadasii* | BT17 | BT05- 0810000017, KJG003 | Wound | C |
| TGC0126 | *C. posadasii* | BT18 | BT05- 0810000018, KJG004 | Wound | C |
| TGC0127 | *C. posadasii* | BT19 | BT05- 0810000019, KJG005 | Pulmonary | C |
| TGC0128 | Unknown | 378 | | lung tissue | |
| TGC0129 | Unknown | 559 | | unknown | |
| TGC0130 | *C. posadasii* | 632 | | unknown | |
| TGC0131 | *C. posadasii* | 633 | | unknown | |
| TGC0132 | *C. posadasii* | 713 | | sputum | |
| TGC0133 | *C. posadasii* | 745 | | unknown | |
| TGC0134 | *C. posadasii* | 1155 | | BAL | |
| TGC0135 | *C. immitis* | 2010 | | Human | C |
| TGC0136 | *C. immitis* | 2012 | RMSCC 2012 | Human | C |
| TGC0137 | *C. posadasii* | 3131 | RMSCC 1038, f0634 | Lung | C |
| TGC0138 | *C. posadasii* | 1042 | RMSCC 1042 | ~ | ~ |
| TGC0139 | *C. immitis* | 2017 | RMSCC 2017 | Human | C |
| TGC0140 | *C. posadasii* | 3142 | RMSCC 1049, f0925 | Cerebral spinal fluid | C |
| TGC0141 | *C. immitis* | 2271 | RMSCC 2271 | Human | C |
| TGC0142 | *C. posadasii* | 3137 | RMSCC 1054 | Urine, CSF | C |
| TGC0143 | *C. immitis* | 3505 | RMSCC 3505 | Human | C |
| TGC0144 | *C. posadasii* | 3101 | RMSCC 1439, f1053 | Sputum | C |
| TGC0145 | *C. posadasii* | 113 | | lymph node | |
| TGC0146 | Unknown | 561 | | unknown | |
| TGC0147 | *C. posadasii* | 114 | | RL Bx | |
| TGC0148 | *C. posadasii* | 211 | | sputum | |
| TGC0149 | *C. posadasii* | 223 | | RUL mass | |
| TGC0150 | *C. posadasii* | 660 | | LL mass | |
| TGC0151 | *C. posadasii* | 5783 | | lung mass | |
| TGC0152 | *C. posadasii* | 3570 | | bronch wash | |
| TGC0153 | *C. posadasii* | 6452 | ID05- 1860006452, KJH004d | Sputum | C |
| TGC0154 | *C. posadasii* | 6453 | ID05- 1860006453, KJH005d | Bronchial wash | C |
| TGC0155 | *C. posadasii* | 6472 | ID05- 1870006472, KJA009 | Bronchial wash | C |
| TGC0156 | *C. posadasii* | 6826 | ID05- 1990006826, KJE003 | Bronchial wash | C |
| TGC0157 | *C. posadasii* | 6831 | ID05- 1990006831, KJD004 | Testicular Abscess | C |
| TGC0158 | *C. posadasii* | 6994 | ID05- 2030006994, KJB008 | Pleural fluid | C |
| TGC0159 | *C. posadasii* | 7471 | ID05-2200007471 | Lung tissue | C |
| TGC0160 | *C. posadasii* | 7527 | ID05- 2210007527, KJC009 | Pulmonary | C |
| TGC0173 | *C. posadasii* | ID05-10154 | | | |
| TGC0174 | Unknown | PT523004/ PT323004 | | | |
| TGC0175 | *C. posadasii* | PT318013 | | | |
| TGC0176 | *C. posadasii* | PT07291021 | | | |
| TGC0177 | *C. posadasii* | PT07290023 | | | |

TABLE 10-continued

Isolate gDNA (whole genome amplified) screened with CocciDxQ assay. A subset of these samples (n = 94) was screened with CocciEnv assay. For origin, C = clinical and E = environmental.

| TGC ID# | Species ID | Strain ID | RMSCC#/Alternate ID | Isolation/Disease Information Source | Origin |
|---|---|---|---|---|---|
| TGC0178 | *C. posadasii* | PT320028 | | | |
| TGC0179 | *C. posadasii* | PT299001 | | | |
| TGC0180 | Unknown | PT07288010 | | | |
| TGC0181 | *C. posadasii* | PT299006 | | | |
| TGC0182 | Unknown | PT305012 | | | |
| TGC0183 | *C. posadasii* | PT305013 | | | |
| TGC0184 | Unknown | PT07292005 | | | |
| TGC0185 | Unknown | PT312004 | | | |
| TGC0186 | Unknown | PT296022 | | | |
| TGC0187 | Unknown | PT07292004 | | | |
| TGC0188 | Unknown | PT07250001 | | | |
| TGC0189 | *C. posadasii* | PT07269001 | | | |
| TGC0190 | *C. posadasii* | PT07270023 | | | |
| TGC0191 | *C. posadasii* | PT07276015 | | | |
| TGC0192 | Unknown | PT298017/ PT268017 | | | |
| TGC0193 | Unknown | PT07250037/ PT07250032 | | | |
| TGC0194 | Unknown | PT324006 | | | |
| TGC0195 | *C. posadasii* | PT296001 | | | |
| TGC0196 | *C. posadasii* | PT07254016 | | | |
| TGC0197 | *C. posadasii* | PT07268016 | | | |
| TGC0198 | Unknown | PT07260017 | | | |
| TGC0199 | *C. posadasii* | PT07291022 | | | |
| TGC0200 | Unknown | PT07290022 | | | |
| TGC0201 | *C. posadasii* | PT295029 | | | |
| TGC0202 | *C. posadasii* | PT268018 | | | |
| TGC0203 | *C. posadasii* | PT309005 | | | |
| TGC0204 | Unknown | PT305014 | | | |
| TGC0205 | *C. posadasii* | PT07278010 | | | |
| TGC0206 | Unknown | PT305010 | | | |
| TGC0207 | Unknown | PT309003 | | | |
| TGC0208 | *C. posadasii* | PT303019 | | | |
| TGC0209 | *C. posadasii* | PT305011 | | | |
| TGC0210 | *C. posadasii* | PT306003 | | | |
| TGC0211 | *C. posadasii* | 3196 | f1202 | Shoulder | C |
| TGC0212 | *C. posadasii* | 3215 | f1132 | Skin biopsy | C |
| TGC0213 | *C. immitis* | 3377 | RMSCC 3377 | Human | C |
| TGC0214 | *C. posadasii* | VFC040 | F0777 | Lung tissue | C |
| TGC0216 | *C. immitis* | 3476 | | | |
| TGC0217 | *C. posadasii* | 3351 | f0675 | Blood | C |
| TGC0218 | *C. posadasii* | 3177 | f1281 | Bronchoalveolar lavage | C |
| TGC0219 | *C. posadasii* | 3251 | f0961 | Lung | C |
| TGC0220 | *C. posadasii* | 3322 | f1002 | Elbow abcess fluid | C |
| TGC0221 | *C. posadasii* | 3315 | f0940 | Lung | C |
| TGC0222 | *C. posadasii* | 3232 | f1244 | Sputum | C |
| TGC0223 | *C. posadasii* | VFC013 | FF512 | Sputum | C |
| TGC0224 | *C. posadasii* | 3474 | f0106 | Lung lesion | C |
| TGC0226 | *C. posadasii* | 3250 | f0960 | Blood | C |
| TGC0227 | *C. posadasii* | 3312 | RMSCC 3312 | ~ | ~ |
| TGC0228 | *C. posadasii* | 3492 | f0813 | Bronch trans | C |
| TGC0229 | *C. posadasii* | 3311 | RMSCC 3311 | ~ | ~ |
| TGC0230 | *C. posadasii* | 3278 | f1070 | Sputum | C |
| TGC0231 | *C. posadasii* | 3317 | f0944 | Blood | C |
| TGC0232 | *C. posadasii* | 3248 | f0953 | TGH mold iso | C |
| TGC0233 | *C. posadasii* | 3247 | | Human | C |
| TGC0234 | *C. posadasii* | 3268 | f1037 | Blood | C |
| TGC0235 | *C. posadasii* | 3262 | f1020 | Bronchoalveolar lavage | C |
| TGC0236 | *C. posadasii* | 3275 | f1066 | Lung | C |
| TGC0237 | *C. posadasii* | 3234 | f1258 | Bronchoalveolar lavage | C |
| TGC0238 | *C. posadasii* | 3319 | f0994 | Bronchoalveolar lavage | C |
| TGC0239 | *C. posadasii* | 3240 | f1265 | Sputum | C |
| TGC0240 | *C. posadasii* | 3299 | f0875 | Sputum | C |
| TGC0241 | *C. posadasii* | 3256 | f0982 | Bronchoalveolar lavage | C |
| TGC0242 | *C. posadasii* | 3236 | | Human | C |
| TGC0243 | *C. posadasii* | 3272 | f1049 | Lung | C |
| TGC0244 | *C. posadasii* | 3273 | f1062 | Sputum | C |
| TGC0245 | *C. posadasii* | 3239 | f1264 | Sputum | C |
| TGC0246 | *C. posadasii* | 3318 | f0988 | Human | C |

TABLE 10-continued

Isolate gDNA (whole genome amplified) screened with CocciDxQ assay. A subset of these samples (n = 94) was screened with CocciEnv assay. For origin, C = clinical and E = environmental.

| TGC ID# | Species ID | Strain ID | RMSCC#/Alternate ID | Isolation/Disease Information Source | Origin |
|---|---|---|---|---|---|
| TGC0247 | *C. posadasii* | 3286 | | | |
| TGC0248 | *C. posadasii* | 3230 | f1242 | Sputum | C |
| TGC0249 | *C. posadasii* | 10 | 30000010 | Urine | C |
| TGC0250 | *C. posadasii* | 3231 | | Human | C |
| TGC0251 | *C. posadasii* | 3237 | f1262 | Sputum | C |
| TGC0252 | *C. posadasii* | 3305 | f0903 | Lung aspirate | C |
| TGC0253 | *C. posadasii* | 3289 | f0830 | Sputum | C |
| TGC0254 | *C. posadasii* | 3221 | | Human | C |
| TGC0255 | *C. posadasii* | 3294 | | | |
| TGC0256 | *C. posadasii* | 3284 | f0754 | Sputum | C |
| TGC0257 | *C. posadasii* | 3223 | | Human | C |
| TGC0258 | *C. immitis* | 2281 | RMSCC 2281 | ~ | ~ |
| TGC0259 | *C. posadasii* | 3300 | f0876 | Lung aspirate | C |
| TGC0260 | *C. posadasii* | 3482 | f0163 | Brain | C |
| TGC0261 | *C. posadasii* | 3238 | f1263 | Pleural fluid | C |
| TGC0262 | *C. posadasii* | 3263 | f1021 | Lung mold bronch | C |
| TGC0263 | *C. posadasii* | 3224 | f1090 | Bronchial wash | C |
| TGC0264 | *C. posadasii* | 3253 | f0969 | Lung nodule | C |
| TGC0265 | *C. posadasii* | 3211 | f1142 | Blood | C |
| TGC0266 | *C. posadasii* | 3285 | | | |
| TGC0267 | *C. posadasii* | 3214 | f1134 | Lymph node | C |
| TGC0268 | *C. posadasii* | 3308 | f0915 | Human | C |
| TGC0269 | *C. posadasii* | 3252 | f0964 | TGH | C |
| TGC0270 | *C. posadasii* | 3293 | f0848 | Tracheal aspirate | C |
| TGC0271 | *C. posadasii* | 3245 | f1274 | Bronchoalveolar lavage | C |
| TGC0272 | *C. posadasii* | 3213 | f1141 | Sputum | C |
| TGC0273 | *C. posadasii* | 3226 | | Human | C |
| TGC0274 | *C. posadasii* | 3298 | f0874 | Sputum | C |
| TGC0275 | *C. posadasii* | 3219 | f1116 | Bronchial wash | C |
| TGC0276 | *C. posadasii* | 3216 | f1130 | Bronchial | C |
| TGC0277 | *C. posadasii* | 3246 | f1275 | Human | C |
| TGC0278 | *C. posadasii* | 3295 | | Human | C |
| TGC0279 | *C. posadasii* | 3227 | f1239 | Sputum | C |
| TGC0280 | *C. posadasii* | 3277 | | Human | C |
| TGC0281 | *C. posadasii* | 3217 | f1124 | Sputum | C |
| TGC0282 | *C. posadasii* | 3269 | f1040 | Arm | C |
| TGC0283 | *C. posadasii* | 3279 | f1071 | Sputum | C |
| TGC0284 | *C. posadasii* | 3169 | f1294 | Sputum | C |
| TGC0285 | *C. posadasii* | VFC014 | FF532 | Lymph node | C |
| TGC0286 | *C. posadasii* | 3165 | f1306 | Face lesion | C |
| TGC0287 | *C. posadasii* | 3192 | f1215 | Sputum | C |
| TGC0288 | *C. posadasii* | 3205 | f1170 | Bronchoalveolar lavage | C |
| TGC0289 | *C. posadasii* | 3207 | f1159 | Lung aspirate | C |
| TGC0290 | *C. posadasii* | VFC010 | FF180 | Sputum | C |
| TGC0291 | *C. posadasii* | VFC007 | FF877 | Human | C |
| TGC0292 | *C. posadasii* | 3356 | f0691 | Bronchial wash | C |
| TGC0293 | *C. immitis* | 2267 [VFC 052 2267] | RMSCC 2267 | ~ | ~ |
| TGC0294 | *C. posadasii* | VFC008 | FF861 | Sputum | C |
| TGC0295 | *C. posadasii* | VFC005 | FF795 | Sputum | C |
| TGC0296 | *C. posadasii* | VFC024 | FF625 | Forearm fluid | C |
| TGC0297 | *C. posadasii* | VFC022 | FF690 | Sputum | C |
| TGC0298 | *C. posadasii* | 3132 | f1038 | Bronchoalveolar lavage | C |
| TGC0299 | *C. posadasii* | VFC019 | FF616 | Human | C |
| TGC0300 | *C. posadasii* | 3199 | f1193 | Pleural tissue | C |
| TGC0301 | *C. posadasii* | 3209 | f1153 | Pleural fluid | C |
| TGC0302 | *C. posadasii* | 3203 | | Human | C |
| TGC0303 | *C. posadasii* | 3357 | f0697 | Sputum | C |
| TGC0304 | *C. posadasii* | 3167 | f1285 | Sputum | C |
| TGC0305 | *C. posadasii* | 3162 | f1300 | Knee fluid | C |
| TGC0306 | *C. posadasii* | 3202 | f1185 | Bronchus | C |
| TGC0307 | *C. posadasii* | VFC006 | FF826 | Bronchial wash | C |
| TGC0308 | *C. posadasii* | 3121 | f0987 | Lung Aspirate | C |
| TGC0309 | *C. immitis* | 3706 | RMSCC 3706 | Human | C |
| TGC0310 | *C. posadasii* | VFC036 | FF538 | Lung | C |
| TGC0311 | *C. posadasii* | VFC047 | 97-300-0319 | Cerebral spinal fluid | C |
| TGC0312 | *C. posadasii* | VFC009 | FF83 | Sputum | C |
| TGC0313 | *C. posadasii* | 3183 | f1234 | Lung | C |
| TGC0314 | *C. posadasii* | VFC029 | FF167 | Abdominal wall tissue | C |

TABLE 10-continued

Isolate gDNA (whole genome amplified) screened with CocciDxQ assay. A subset of these samples (n = 94) was screened with CocciEnv assay. For origin, C = clinical and E = environmental.

| TGC ID# | Species ID | Strain ID | RMSCC#/Alternate ID | Isolation/Disease Information Source | Origin |
|---|---|---|---|---|---|
| TGC0315 | *C. immitis* | 3475 | RMSCC 3475 | ~ | ~ |
| TGC0316 | *C. posadasii* | 3190 | f1219 | Blood | C |
| TGC0317 | *C. posadasii* | VFC011 | FF379 | Lung aspirate | C |
| TGC0318 | *C. posadasii* | 3208 | f1158 | Sputum | C |
| TGC0319 | *C. immitis* | 2008 [VFC 043 2008] | RMSCC 2008, VFC043 | Human | C |
| TGC0320 | *C. posadasii* | VFC030 | FF340 | FNA lung | C |
| TGC0321 | *C. immitis* | 2395 | RMSCC 2395 | Human | C |
| TGC0322 | *C. posadasii* | VFC012 | FF449 | Lung | C |
| TGC0323 | *C. posadasii* | VFC033 | FF387 | Sputum | C |
| TGC0324 | *C. posadasii* | VFC032 | FF368 | Sputum | C |
| TGC0325 | *C. posadasii* | 3355 | f0688 | Bronchial wash | C |
| TGC0326 | *C. posadasii* | VFC021/VFC02 18 | | CAPD fluid | C |
| TGC0327 | *C. posadasii* | 3163 | f1302 | Sputum | C |
| TGC0328 | *C. posadasii* | 3346 | f0656 | Lung tissue | C |
| TGC0329 | *C. posadasii* | 3333 | f0562 | Neck drainage | C |
| TGC0330 | *C. posadasii* | VFC037 | FF612 | Sputum | C |
| TGC0331 | *C. posadasii* | 3193 | f1210 | Blood | C |
| TGC0332 | *C. posadasii* | VFC034 | FF455 | Sputum | C |
| TGC0333 | *C. posadasii* | VFC031 | FF361 | Sputum | C |
| TGC0334 | *C. posadasii* | VFC028 | FF170 | Sputum | C |
| TGC0335 | *C. posadasii* | VFC017 | FF551 | Sputum | C |
| TGC0336 | *C. posadasii* | 3174 | f1277 | Sputum | C |
| TGC0337 | *C. posadasii* | VFC016 | FF555 | Bronchial aveolar lavage | C |
| TGC0338 | *C. posadasii* | VFC025 | FF715 | Sputum | C |
| TGC0339 | *C. posadasii* | 3187 | f1223 | Urine | C |
| TGC0340 | *C. posadasii* | 3491 | f1257 | Human | C |
| TGC0341 | *C. posadasii* | 3457 | f0193 | Skin | C |
| TGC0342 | *C. immitis* | 2279 | RMSCC 2279 | ~ | ~ |
| TGC0343 | *C. immitis* | 2268 | RMSCC 2268 | ~ | ~ |
| TGC0344 | *C. posadasii* | 184 | ID02-184 | Bronchial wash | C |
| TGC0345 | *C. posadasii* | 3409 | f0263 | Sputum | C |
| TGC0346 | *C. posadasii* | VFC020 | FF641 | Lung aspirate | C |
| TGC0347 | *C. posadasii* | VFC002 | FF416 | Human | C |
| TGC0348 | *C. posadasii* | 3175 | f1278 | Human | C |
| TGC0349 | *C. posadasii* | 3395 | f0388 | Blood | C |
| TGC0350 | *C. posadasii* | 587 | id03-587 | Bronchial wash | C |
| TGC0351 | *C. immitis* | 2269 | RMSCC 2269 | ~ | ~ |
| TGC0352 | *C. posadasii* | 3198 | f1194 | Bronchoalveolar lavage | C |
| TGC0353 | *C. posadasii* | VFC003 | FF430 | Bronchial tissue | C |
| TGC0354 | *C. posadasii* | 3172 | f1287 | Lung aspirate | C |
| TGC0355 | *C. posadasii* | 3398 | f0391 | Bronchial wash | C |
| TGC0356 | *C. posadasii* | CPA0085 | a03-6397 | Cat | C |
| TGC0357 | *C. posadasii* | Mar-78 | | | |
| TGC0358 | *C. posadasii* | 3160 | f1298 | Femur | C |
| TGC0359 | *C. posadasii* | 3206 | f1164 | Human | C |
| TGC0360 | *C. posadasii* | 3335 | f0565 | Sputum | C |
| TGC0361 | *C. posadasii* | 3413 | f0269 | Human | C |
| TGC0362 | *C. posadasii* | 3538 | 0204-3538 | Pleural fluid | C |
| TGC0363 | *C. posadasii* | 5786 | 0204-5786 | Bone marrow | C |
| TGC0364 | *C. posadasii* | 3336 | f0577 | Sputum | C |
| TGC0365 | *C. posadasii* | 3168 | f1295 | Bronchoalveolar lavage | C |
| TGC0366 | *C. posadasii* | 3186 | f1224 | Bronchoalveolar lavage | C |
| TGC0367 | *C. posadasii* | 517 | id03-517 | Bronchial wash | C |
| TGC0368 | *C. posadasii* | 584 | id03-584 | Sputum | C |
| TGC0370 | *C. posadasii* | VFC018 | FF584 | Sputum | C |
| TGC0371 | *C. immitis* | 3693 | RMSCC 3693 | ~ | ~ |
| TGC0372 | *C. posadasii* | 3180 | f1266 | Human | C |
| TGC0373 | *C. posadasii* | 5127 | 0205-5127 | Bronchial wash | C |
| TGC0374 | *C. immitis* | 2278 | RMSCC 2278 | ~ | ~ |
| TGC0375 | *C. posadasii* | 3489 | f1222 | Human | C |
| TGC0376 | *C. posadasii* | 3128 [VFC 049] | RMSCC 1036, B3128, f0415, VFC049 | Wound | C |
| TGC0379 | *C. posadasii* | 3411 | f0267 | Bronchus | C |
| TGC0380 | *C. posadasii* | CPA0088 | a03-8172 | Cat | C |
| TGC0381 | *C. immitis* | 2277 | RMSCC 2277 | Human | C |
| TGC0382 | *C. posadasii* | 3201 | f1190 | Bronchoalveolar lavage | C |

TABLE 10-continued

Isolate gDNA (whole genome amplified) screened with CocciDxQ assay. A subset of these samples (n = 94) was screened with CocciEnv assay. For origin, C = clinical and E = environmental.

| TGC ID# | Species ID | Strain ID | RMSCC#/Alternate ID | Isolation/Disease Information Source | Origin |
|---|---|---|---|---|---|
| TGC0383 | *C. posadasii* | 2294 | | | |
| TGC0384 | *C. posadasii* | 3166 | f1309 | Bronchoalveolar lavage | C |
| TGC0385 | *C. posadasii* | 4165 | 0204-4165 | Sputum | C |
| TGC0386 | *C. posadasii* | 9888 | 0204-9888 | Bronchial wash | C |
| TGC0387 | *C. posadasii* | 7892 | 0204-7892 | Sputum | C |
| TGC0388 | *C. posadasii* | 3157 | RMSCC 1040 | Bronchoalveolar lavage | C |
| TGC0389 | *C. posadasii* | 3488 | RMSCC 3488 | Human | C |
| TGC0390 | *C. posadasii* | C735 | | Lab Strain, Patient isolation | C |
| TGC0391 | *C. posadasii* | Silveira | | Lab Strain, Patient isolation | C |
| TGC0392 | *C. posadasii* | CPA0066 | 604-1 L | Soil | E |
| TGC0393 | *C. immitis* | RS | | Vaccine/Lab Strain, Patient isolation | C |
| TGC0394 | *C. posadasii* | 3310 | f0920 | Sputum | C |
| TGC0395 | *C. posadasii* | 3314 | f0939 | TTA | C |
| TGC0396 | *C. posadasii* | 3145 | RMSCC 1037 | Skin biopsy | C |
| TGC0398 | *C. posadasii* | 2133 | RMSCC 2133 | Human | C |
| TGC0399 | *C. posadasii* | CPA0020 | 485B-0 L | Soil | E |
| TGC0400 | *C. immitis* | 2394 | RMSCC 2394 | Human | C |
| TGC0401 | *C. posadasii* | CPA0001 | 407-0 L | Soil | E |
| TGC0402 | *C. immitis* | 3703 | RMSCC 3703 | Human | C |
| TGC0403 | *C. immitis* | 2014 | RMSCC 2014 | ~ | ~ |
| TGC0405 | *C. posadasii* | 3290 | f0931 | Sputum | C |
| TGC0406 | *C. posadasii* | 3352 | f0676 | Sputum | C |
| TGC0408 | *C. posadasii* | 3301 | f0877 | Bronchoalveolar lavage | C |
| TGC0409 | *C. posadasii* | 3220 | f1107 | Lung biopsy | C |
| TGC0410 | *C. posadasii* | 3244 | f1273 | Bronchoalveolar lavage | C |
| TGC0413 | *C. immitis* | 2009 | RMSCC 2009 | ~ | ~ |
| TGC0414 | *C. posadasii* | 3283 | f1087 | Sputum | C |
| TGC0415 | *C. posadasii* | 3243 | f1270 | Bone marrow | C |
| TGC0416 | *C. immitis* | 2274 | RMSCC 2274 | ~ | ~ |
| TGC0417 | *C. posadasii* | 3276 | f1067 | Bronchoalveolar lavage | C |
| TGC0418 | *C. posadasii* | 3222 | | Human | C |
| TGC0419 | *C. posadasii* | 3321 | | Human | C |
| TGC0420 | *C. posadasii* | 3233 | f1247 | Pleural fluid | C |
| TGC0421 | *C. posadasii* | 3228 | f1240 | Lung | C |
| TGC0422 | *C. posadasii* | 3291 | f0832 | Sputum | C |
| TGC0423 | *C. posadasii* | 3229 | f1241 | Tissue mass | C |
| TGC0424 | *C. posadasii* | 3292 | f0843 | Sputum | C |
| TGC0425 | *C. posadasii* | 3354 | f0687 | Skin biopsy | C |
| TGC0426 | *C. immitis* | 2280 | RMSCC 2280 | ~ | ~ |
| TGC0427 | *C. posadasii* | 3326 | f0537 | Lung nodule | C |
| TGC0428 | *C. posadasii* | 3296 | | Human | C |
| TGC0429 | *C. immitis* | 2015 | RMSCC 2015 | ~ | ~ |
| TGC0430 | *C. immitis* | 2273 | RMSCC 2273 | ~ | ~ |
| TGC0431 | *C. posadasii* | 3249 | f0956 | Bronchus | C |
| TGC0432 | *C. posadasii* | 3313 | f0936 | SE | C |
| TGC0434 | *C. immitis* | 2011 | RMSCC 2011 | ~ | ~ |
| TGC0435 | *C. posadasii* | 3353 | f0678 | Bronchial wash | C |
| TGC0436 | *C. posadasii* | 3344 | f0650 | Bronchial wash | C |
| TGC0437 | *C. posadasii* | 3184 | f1233 | Thoracentesis | C |
| TGC0438 | *C. posadasii* | 3210 | f1143 | Bronchoalveolar lavage | C |
| TGC0439 | *C. posadasii* | VFC038 | FF569 | Pleural fluid | C |
| TGC0440 | *C. posadasii* | 3161 | f1299 | Lung | C |
| TGC0441 | *C. posadasii* | 3185 | f1232 | Lung aspirate | C |
| TGC0442 | *C. posadasii* | 3197 | f1196 | Lung biopsy | C |
| TGC0443 | *C. posadasii* | 3181 | f1236 | Sputum | C |
| TGC0444 | *C. posadasii* | 2372 | | | |
| TGC0445 | *C. posadasii* | 3191 | f1217 | Lung biopsy | C |
| TGC0446 | *C. posadasii* | VFC039 | FF670 | Sputum | C |
| TGC0447 | *C. immitis* | 3705 | RMSCC 3705 | ~ | ~ |
| TGC0448 | *C. posadasii* | 3375 | f0339 | Lung biopsy | C |
| TGC0449 | *C. posadasii* | 3348 | f0664 | Lung aspirate | C |
| TGC0450 | *C. posadasii* | 3178 | f1282 | Bronchoalveolar lavage | C |
| TGC0451 | *C. posadasii* | 3350 | | Human | C |
| TGC0452 | *C. posadasii* | 3188 | f1221 | Sputum | C |

TABLE 10-continued

Isolate gDNA (whole genome amplified) screened with CocciDxQ assay. A subset of these samples (n = 94) was screened with CocciEnv assay. For origin, C = clinical and E = environmental.

| TGC ID# | Species ID | Strain ID | RMSCC#/Alternate ID | Isolation/Disease Information Source | Origin |
|---|---|---|---|---|---|
| TGC0453 | *C. posadasii* | 3347 | f0658 | Trans bronch biopsy | C |
| TGC0455 | *C. immitis* | 2105 | RMSCC 2105, VFC050 | Human | C |
| TGC0456 | *C. immitis* | 2006 | RMSCC 2006 | ~ | ~ |
| TGC0457 | *C. posadasii* | 3349 | | Human | C |
| TGC0458 | *C. posadasii* | 3171 | f1289 | Sputum | C |
| TGC0459 | *C. posadasii* | VFC057 | KUM4825 | Abdominal wall tissue | C |
| TGC0460 | *C. posadasii* | 3139 | f1010 | Sputum | C |
| TGC0461 | *C. posadasii* | 3170 | f1293 | Sputum | C |
| TGC0462 | *C. posadasii* | CPA0087 | a03-7777 | Dog | C |
| TGC0463 | *C. posadasii* | 2127 | RMSCC 2127, VFC041 | Human | C |
| TGC0464 | *C. posadasii* | 3179 | f1283 | Joint fluid | C |
| TGC0465 | *C. immitis* | 2102 | RMSCC 2102 | ~ | ~ |
| TGC0466 | *C. posadasii* | VFC001 | F415 | Forehead lesion aspirate | C |
| TGC0467 | *C. posadasii* | 3164 | f1305 | Sputum | C |
| TGC0469 | *C. posadasii* | 3136 | f1133 | Sputum | C |
| TGC0470 | *C. posadasii* | 3200 | f1192 | Urine | C |
| TGC0471 | *C. immitis* | 2275 | RMSCC 2275 | Human | C |
| TGC0472 | *C. posadasii* | 8959 | 0204-8959 | Bronchial wash | C |
| TGC0473 | *C. immitis* | 2276 | RMSCC 2276 | ~ | ~ |
| TGC0474 | *C. posadasii* | 59 | ID02-59 | Lung biopsy | C |
| TGC0475 | *C. posadasii* | 3490 | f1256 | Lung | C |
| TGC0476 | *C. posadasii* | 927 | id03-927 | Lung biopsy | C |
| TGC0477 | *C. immitis* | 3479 | RMSCC 3479 | Human | C |
| TGC0478 | *C. posadasii* | 1D02-60 | | | |
| TGC0480 | *C. posadasii* | 3374 | f0337 | Skin biopsy | C |
| TGC0481 | *C. posadasii* | 3338 | 0205-3338 | Bronchial wash | C |
| TGC0482 | *C. posadasii* | 3381 | f0353 | Sputum | C |
| TGC0483 | *C. posadasii* | 3368 | f0328 | Lung | C |
| TGC0484 | *C. posadasii* | 3129 | 0205-3129 | Wound | C |
| TGC0485 | *C. posadasii* | 4885 | 0205-4885 | Bronchial wash | C |
| TGC0486 | *C. posadasii* | 3420 | f0280 | Pleural fluid | C |
| TGC0487 | *C. posadasii* | Mar-87 | | | |
| TGC0488 | *C. posadasii* | 3440 | f0322 | Human | C |
| TGC0489 | *C. posadasii* | CPA0086 | a03-7379 | Llama | C |
| TGC0490 | *C. posadasii* | 674 | id03-674 | Lung nodule | C |
| TGC0492 | *C. posadasii* | 49 | ID02-49 | Bone marrow | C |
| TGC0493 | *C. posadasii* | 699 | id03-699 | Bronchoalveolar lavage | C |
| TGC0494 | *C. posadasii* | 3364 | f0738 | Shoulder | C |
| TGC0495 | *C. posadasii* | 179 | ID03-179 | Sputum | C |
| TGC0496 | *C. posadasii* | 8157 | 0204-8157 | Bronchial wash | C |
| TGC0497 | *C. posadasii* | 7874/0204-7074 | 0204-7874 | Bronchial wash | C |
| TGC0498 | *C. posadasii* | 9968 | 0203-9968 | Bronchial wash | C |
| TGC0499 | *C. posadasii* | CPA0083 | a03-4364 | Cat | C |
| TGC0500 | *C. posadasii* | 8174 | 0204-8174 | Chest fluid | C |
| TGC0501 | *C. posadasii* | 3391 | | | |
| TGC0502 | *C. posadasii* | 3417 | f0276 | Bronchial wash | C |
| TGC0503 | *C. posadasii* | 147 | ID02-147 | Bronchial wash | C |
| TGC0504 | *C. posadasii* | 3447 | f0079 | Urine | C |
| TGC0505 | *C. posadasii* | h20289 | | Human | C |
| TGC0506 | *C. posadasii* | 8911 | 0205-8911 | Blood | C |
| TGC0507 | *C. posadasii* | 263 | ID02-263 | Sputum | C |
| TGC0508 | *C. posadasii* | 3439 | f0321 | Human | C |
| TGC0509 | *C. posadasii* | 3360 | f0718 | Sputum | C |
| TGC0511 | *C. posadasii* | 3341 | f0591 | Sputum | C |
| TGC0512 | *C. posadasii* | 3345 | f0652 | Bone marrow | C |
| TGC0513 | *C. posadasii* | 7076 | 0204-7076 | Lung tissue | C |
| TGC0514 | *C. posadasii* | 3358 | f0700 | Bronchial wash | C |
| TGC0515 | *C. immitis* | 3382 | f0354 | Gastric aspirate | C |
| TGC0517 | *C. posadasii* | PT08141001 | | Forehead Wound | C |
| TGC0518 | *C. posadasii* | PT08140024 | | Bronch Wash | C |
| TGC0519 | Unknown | PT08164001 | | Bronch Wash | C |
| TGC0520 | *C. posadasii* | PT08148001 | | Bronch Wash | C |
| TGC0521 | Unknown | PT08172013 | | Bronch Wash | C |
| TGC0522 | *C. posadasii* | PT08140028 | | BAL | C |
| TGC0523 | *C. posadasii* | PT08128012 | | Bronch Wash | C |
| TGC0524 | *C. posadasii* | PT08129008 | | CSF | C |
| TGC0525 | *C. posadasii* | PT08126016 | | Sputum | C |
| TGC0526 | *C. posadasii* | PT08137008 | | Sputum | C |
| TGC0527 | *C. posadasii* | PT08084019 | | Pleural Fluid | C |
| TGC0528 | *C. posadasii* | PT08091007 | | Bronch Wash | C |
| TGC0529 | Unknown | PT08115001 | | Bronch Wash | C |

TABLE 10-continued

Isolate gDNA (whole genome amplified) screened with CocciDxQ assay. A subset of these samples (n = 94) was screened with CocciEnv assay. For origin, C = clinical and E = environmental.

| TGC ID# | Species ID | Strain ID | RMSCC#/Alternate ID | Isolation/Disease Information Source | Origin |
|---|---|---|---|---|---|
| TGC0530 | Unknown | PT08103001 | | Sputum | C |
| TGC0531 | Unknown | PT08099015 | | Bronch Wash | C |
| TGC0532 | Unknown | PT08100013 | | R. Chest tissue | C |
| TGC0533 | Unknown | PT08189001 | | Bronch Wash | C |
| TGC0534 | Unknown | PT08196009 | | Hip Joint | C |
| TGC0535 | Unknown | PT08192009 | | Sputum | C |
| TGC0536 | Unknown | PT08200005 | | R. Upper Lung | C |
| TGC0537 | Unknown | PT08172014 | | Bronch Wash | C |
| TGC0538 | Unknown | PT08189002 | | Bronch Wash | C |
| TGC0539 | Unknown | PT08179006 | | Left lung | C |
| TGC0540 | Unknown | PT08171012 | | BAL | C |
| TGC0541 | Unknown | PT08224005 | | Rigth lung mass | C |
| TGC0542 | Unknown | PT08205002 | | Bronch Wash | C |
| TGC0543 | Unknown | PT08206002 | | Bronch Swab | C |
| TGC0544 | Unknown | PT08200006 | | Bronch Wash | C |
| TGC0545 | Unknown | PT08224008 | | Bronch | C |
| TGC0546 | Unknown | PT08217008 | | Bronch Wash | C |
| TGC0547 | Unknown | PT08226004 | | Unknown | C |
| TGC0548 | Unknown | PT08203016 | | Sputum | C |
| TGC0552 | Unknown | PT08240019 | | Sputum | |
| TGC0553 | Unknown | PT08228008 | | Abscess, back | |
| TGC0554 | Unknown | PT08235003 | | Sputum | |
| TGC0555 | Unknown | PT08219008 | | Sputum | |
| TGC0556 | Unknown | PT08228009 | | Leg Wound | |
| TGC0557 | Unknown | PT08256022 | | Bronch Wash | |
| TGC0558 | Unknown | PT08231010 | | Lymph Node | |
| TGC0559 | Unknown | PT08197007 | | BAL | |
| TGC0560 | Unknown | PT08256023 | | Sputum | |
| TGC0561 | Unknown | PT08169002 | | Knee | |
| TGC0562 | Unknown | PT08266012 | | Right Lower Lung | |
| TGC0563 | Unknown | PT08267009 | | BAL | |
| TGC0564 | Unknown | PT08246015 | | CSF | |
| TGC0565 | Unknown | TG06812 | | Sputum | |
| TGC0566 | Unknown | TG6480 | | Sputum | |
| TGC0567 | Unknown | PT08288016 | | | |
| TGC0568 | Unknown | PT08297002 | | | |
| TGC0569 | Unknown | PT08297001 | | | |
| TGC0570 | Unknown | PT08294003 | | | |
| TGC0571 | Unknown | PT08301009 | | | |
| TGC0572 | Unknown | PT08302004 | | | |
| TGC0573 | Unknown | PT08301010 | | | |
| TGC0574 | Unknown | PT08303030 | | | |
| TGC0575 | Unknown | PT08288012 | | | |
| TGC0576 | Unknown | PT08303031 | | | |
| TGC0577 | Unknown | PT08284003 | | | |
| TGC0578 | Unknown | PT08283001 | | | |
| TGC0579 | Unknown | PT08288010 | | | |
| TGC0580 | Unknown | PT08319002 | | | |
| TGC0581 | Unknown | PT08304014 | | | |
| TGC0582 | Unknown | PT08288009 | | | |
| TGC0583 | Unknown | PT08246023 | | | |
| TGC0584 | Unknown | PT08308015 | | | |
| TGC0585 | Unknown | PT08283003 | | | |
| TGC0586 | Unknown | PT08246025 | | | |
| TGC0587 | Unknown | PT08246024 | | | |
| TGC0588 | Unknown | PT08246016 | | | |
| TGC0589 | *C. immitis* | CDCtransplant1 | | | C |
| TGC0590 | *C. immitis* | CDCtransplant2 | | | C |
| TGC0591 | *C. immitis* | CDCtransplant3 | | | C |
| TGC0648 | *C. posadasii* | 2343 | RMSCC 2343 | ~ | ~ |
| TGC0649 | *C. posadasii* | 2346 | RMSCC 2346 | ~ | ~ |
| TGC0650 | *C. posadasii* | 3472 | RMSCC 3472 | ~ | ~ |
| TGC0651 | *C. posadasii* | 3480 | RMSCC 3480 | ~ | ~ |
| TGC0652 | *C. posadasii* | 3487 | RMSCC 3487 | ~ | ~ |
| TGC0655 | *C. posadasii* | 3506 | RMSCC 3506 | ~ | ~ |

Additionally, a direct comparison of CocciEnv and CocciDxQ showed that the CocciEnv assay results in an average of 1.81 and range of 1.56 to 2.05 in Ct values earlier than that from the CocciDxQ assay when screened on the same DNA (Table 11). This translates to an almost 4-fold higher capture of *Coccidioides* DNA in a sample.

TABLE 11

Coccidioides genomic DNA screened for a side-by-side comparison of the CocciDxQ and CocciEnv assays.

| Sample (in duplicate) | CocciEnv qPCR Ct value | CocciDxQ qPCR Ct value | Ct value difference between CocciEnv and CocciDxQ |
|---|---|---|---|
| TGC0004_1-3 | 21.18 | 22.92 | 1.74 |
| TGC0004_1-3 | 21.09 | 22.93 | 1.85 |
| TGC0213_1-3 | 21.37 | 23.14 | 1.77 |
| TGC0213_1-3 | 21.32 | 23.12 | 1.80 |
| TGC0222_1-3 | 21.17 | 23.00 | 1.83 |
| TGC0222_1-3 | 21.22 | 23.05 | 1.83 |
| TGC0293_1-3 | 19.24 | 21.11 | 1.88 |
| TGC0293_1-3 | 19.28 | 21.20 | 1.92 |
| TGC0306_1-3 | 19.38 | 21.27 | 1.89 |
| TGC0306_1-3 | 19.30 | 21.24 | 1.95 |
| TGC0319_1-3 | 16.75 | 18.66 | 1.90 |
| TGC0319_1-3 | 16.80 | 18.50 | 1.70 |
| TGC0332_1-3 | 17.68 | 19.66 | 1.98 |
| TGC0332_1-3 | 17.67 | 19.64 | 1.97 |
| TGC0350_1-3 | 18.57 | 20.57 | 2.00 |
| TGC0350_1-3 | 18.49 | 20.54 | 2.05 |
| TGC0385_1-3 | 17.31 | 19.30 | 2.00 |
| TGC0385_1-3 | 17.25 | 19.28 | 2.03 |
| TGC0392_1-3 | 26.49 | 28.46 | 1.97 |
| TGC0392_1-3 | 26.49 | 28.43 | 1.94 |
| TGC0396_1-3 | 19.00 | 20.98 | 1.97 |
| TGC0396_1-3 | 18.85 | 20.91 | 2.06 |
| TGC0404_1-3 | 14.60 | 16.56 | 1.96 |
| TGC0404_1-3 | 14.68 | 16.50 | 1.82 |
| TGC0408_1-3 | 18.90 | 20.61 | 1.71 |
| TGC0408_1-3 | 18.85 | 20.60 | 1.75 |
| TGC0434_1-3 | 16.97 | 18.58 | 1.61 |
| TGC0434_1-3 | 16.99 | 18.55 | 1.56 |
| TGC0442_1-3 | 20.58 | 22.21 | 1.63 |
| TGC0442_1-3 | 20.62 | 22.20 | 1.58 |
| TGC0450_1-3 | 19.79 | 21.50 | 1.70 |
| TGC0450_1-3 | 19.81 | 21.53 | 1.72 |
| TGC0453_1-3 | 17.98 | 19.81 | 1.83 |
| TGC0453_1-3 | 17.91 | 19.81 | 1.90 |
| TGC0458_1-3 | 19.98 | 21.58 | 1.61 |
| TGC0458_1-3 | 19.81 | 21.57 | 1.76 |
| TGC0467_1-3 | 20.09 | 21.82 | 1.73 |
| TGC0467_1-3 | 20.02 | 21.81 | 1.79 |
| TGC0470_1-3 | 18.90 | 20.68 | 1.78 |
| TGC0470_1-3 | 18.91 | 20.55 | 1.64 |
| TGC0473_1-3 | 20.74 | 22.42 | 1.67 |
| TGC0473_1-3 | 20.77 | 22.35 | 1.58 |
| TGC0478_1-3 | 17.64 | 19.25 | 1.61 |
| TGC0478_1-3 | 17.65 | 19.30 | 1.65 |
| TGC0528_1-3 | 35.12 | 36.79 | 1.66 |
| TGC0528_1-3 | Negative | 36.91 | |
| Average no. cycles of earlier amplification of gDNA with CocciEnv versus CocciDxQ assay | | | 1.81 |

We claim:

1. A method of detecting *Coccidioides* in a DNA-containing sample comprising the steps of:

adding a first and a second oligonucleotide capable of binding SEQ ID NO. 1 to a mixture comprising the DNA-containing sample, wherein the first oligonucleotide includes at least one sequence selected from the group consisting of SEQ ID NOs: 10-14 and oligonucleotides having at least 90% sequence identity to any one of SEQ ID NOs: 10-14, wherein the second oligonucleotide includes at least one sequence selected from the group consisting of SEQ ID NOs: 21-27, 32, and 34, and oligonucleotides having at least 90% sequence identity to any one of SEQ ID NOs: 21-27, 32, and 34;

subjecting the mixture containing the first and second oligonucleotides to conditions that allow amplification of nucleic acid comprising the first oligonucleotide;

and detecting whether *Coccidioides* is present in the DNA-containing sample by detecting nucleic acid amplification of *Coccidioides* DNA.

2. The method of claim 1, wherein the result comprises a Ct value.

3. The method of claim 1, wherein the first oligonucleotide is capable of hybridizing with complements of SEQ ID NO: 10, and the second oligonucleotide is capable of hybridizing with complements of SEQ ID NO: 21 in the mixture.

4. The method of claim 1, further comprising the step of adding a third oligonucleotide to the mixture, wherein the third oligonucleotide binds to its complement included in the amplification products by the first and second oligonucleotides.

5. The method of claim 4, wherein the third oligonucleotide includes a sequence selected from the group consisting of SEQ ID NO. 2 and oligonucleotides having at least 90% sequence identity to SEQ ID NO. 2.

6. The method of claim 4, wherein at least one of the first, the second and the third oligonucleotides comprises a label.

7. The method of claim 6, wherein the label comprises a fluorescent label.

8. The methods of claim 6, wherein the third oligonucleotide comprises a fluorescent label.

9. The method of claim 1, further comprising the step of isolating DNA from the DNA-containing sample.

10. The method of claim 1, wherein the sample comprises an environmental sample.

11. The method of claim 10, wherein the environmental sample comprises a soil sample.

12. The method of claim 1, wherein the sample is derived from a subject.

13. The method of claim 12, wherein the subject is selected from the group consisting of a human, a companion animal, a domesticated animal, a livestock animal, and a wild animal species.

14. A method of quantifying *Coccidioides* in a DNA-containing sample comprising the steps of:

adding a first and a second oligonucleotide capable of binding SEQ ID NO. 1 to a mixture comprising the DNA-containing sample, wherein the first oligonucleotide includes at least one sequence selected from the group consisting of SEQ ID NOs: 10-14 and oligonucleotides having at least 90% sequence identity to any one of SEQ ID NOs: 10-14, wherein the second oligonucleotide includes at least one sequence selected from the group comprising consisting of SEQ ID NOs: 21-27, 32, and 34, and oligonucleotides having at least 90% sequence identity to any one of SEQ ID NOs: 21-27, 32, and 34;

subjecting the mixture containing the first and second oligonucleotides to conditions that allow amplification of a template DNA comprising the first oligonucleotide;

and detecting the amount of *Coccidioides* DNA in the sample based on the relative quantity of *Coccidioides* DNA amplification to a reference result.

15. The method of claim 14, wherein the reference result is obtained by amplification of a DNA-containing sample having a known quantity of *Coccidioides.*

16. The method of claim 14, wherein the reference result is predetermined.

17. The method of claim 14, wherein the first and the reference result each comprises a Ct value.

18. The method of claim 14, further comprising the step of adding a third oligonucleotide to the mixture, wherein the third oligonucleotide binds to its complement included in the amplification products by the first and second oligonucleotides.

19. The method of claim 18, wherein the third oligonucleotide includes a sequence selected from the group consisting of SEQ ID NO. 2 and oligonucleotides having at least 90% sequence identity to SEQ ID NO: 2.

20. The method of claim 18, wherein at least one of the first, the second, and the third oligonucleotides comprises a label.

21. The method of claim 20, wherein the label comprises a fluorescent label.

22. The method of claim 20, wherein the third oligonucleotide comprises a fluorescent label.

23. The method of claim 14, further comprising the step of isolating DNA from the DNA-containing sample.

24. The method of claim 14, wherein the sample comprises an environmental sample.

25. The method of claim 24, wherein the environmental sample comprises a soil sample.

26. The method of claim 14, wherein the sample is derived from a subject, and further wherein the subject is selected from the group consisting of a human, a companion animal, a domesticated animal, a livestock animal, and a wild animal species.

* * * * *

SEQUENCE LISTING

```
<160> NUMBER OF SEQ ID NOS: 38

<210> SEQ ID NO 1
<211> LENGTH: 104
<212> TYPE: DNA
<213> ORGANISM: Coccidioides

<400> SEQUENCE: 1

tgttaggtaa tccaactagc acctcgctca cgtgacccac atagattagc cgagattccc      60

ctttaggtag cttagtgaat gacaagcata caagtcctcc atca                     104


<210> SEQ ID NO 2
<211> LENGTH: 16
<212> TYPE: DNA
<213> ORGANISM: Artificial Sequence
<220> FEATURE:
<223> OTHER INFORMATION: probe

<400> SEQUENCE: 2

acccacatag attagc                                                     16


<210> SEQ ID NO 3
<211> LENGTH: 25
<212> TYPE: DNA
<213> ORGANISM: Artificial Sequence
<220> FEATURE:
<223> OTHER INFORMATION: primer or probe

<400> SEQUENCE: 3

gtgttaggta gtccaactag cacct                                           25
```

-continued

<210> SEQ ID NO 4
<211> LENGTH: 25
<212> TYPE: DNA
<213> ORGANISM: Artificial Sequence
<220> FEATURE:
<223> OTHER INFORMATION: primer or probe

<400> SEQUENCE: 4
gtgttaggta atccaaccag cacct 25

<210> SEQ ID NO 5
<211> LENGTH: 25
<212> TYPE: DNA
<213> ORGANISM: Artificial Sequence
<220> FEATURE:
<223> OTHER INFORMATION: primer or probe

<400> SEQUENCE: 5
gtgttaggta atccaactag cacct 25

<210> SEQ ID NO 6
<211> LENGTH: 24
<212> TYPE: DNA
<213> ORGANISM: Artificial Sequence
<220> FEATURE:
<223> OTHER INFORMATION: primer or probe

<400> SEQUENCE: 6
ctgatggagg actcgtatgc ttgt 24

<210> SEQ ID NO 7
<211> LENGTH: 24
<212> TYPE: DNA
<213> ORGANISM: Artificial Sequence
<220> FEATURE:
<223> OTHER INFORMATION: primer or probe

<400> SEQUENCE: 7
ctgatggagg acttgtacac ttgt 24

<210> SEQ ID NO 8
<211> LENGTH: 24
<212> TYPE: DNA
<213> ORGANISM: Artificial Sequence
<220> FEATURE:
<223> OTHER INFORMATION: primer or probe

<400> SEQUENCE: 8
ctgatggagg aattgtatgc ttgt 24

<210> SEQ ID NO 9
<211> LENGTH: 24
<212> TYPE: DNA
<213> ORGANISM: Artificial Sequence
<220> FEATURE:
<223> OTHER INFORMATION: primer or probe

<400> SEQUENCE: 9
ctgatggagg acttgtatgc ttgt 24

<210> SEQ ID NO 10
<211> LENGTH: 19
<212> TYPE: DNA
<213> ORGANISM: Artificial Sequence
<220> FEATURE:
<223> OTHER INFORMATION: primer or probe

<400> SEQUENCE: 10
cgttgcacrg ggagcacct 19

<210> SEQ ID NO 11
<211> LENGTH: 23
<212> TYPE: DNA
<213> ORGANISM: Artificial Sequence
<220> FEATURE:
<223> OTHER INFORMATION: primer or probe

<400> SEQUENCE: 11
aagctttgga tctttgtggc tct 23

<210> SEQ ID NO 12
<211> LENGTH: 22
<212> TYPE: DNA
<213> ORGANISM: Artificial Sequence
<220> FEATURE:
<223> OTHER INFORMATION: primer or probe

<400> SEQUENCE: 12
aattgatcca ttgcaagcac ct 22

<210> SEQ ID NO 13
<211> LENGTH: 24
<212> TYPE: DNA
<213> ORGANISM: Artificial Sequence
<220> FEATURE:
<223> OTHER INFORMATION: primer or probe

<400> SEQUENCE: 13
aatccaacct ttggaactac acct 24

<210> SEQ ID NO 14
<211> LENGTH: 23
<212> TYPE: DNA
<213> ORGANISM: Artificial Sequence
<220> FEATURE:
<223> OTHER INFORMATION: primer or probe

<400> SEQUENCE: 14
ttttccggta tggactagca cct 23

<210> SEQ ID NO 15
<211> LENGTH: 24
<212> TYPE: DNA
<213> ORGANISM: Artificial Sequence
<220> FEATURE:
<223> OTHER INFORMATION: primer or probe

<400> SEQUENCE: 15
tgttaggtaa tcyaacyagc acct 24

<210> SEQ ID NO 16
<211> LENGTH: 24
<212> TYPE: DNA
<213> ORGANISM: Artificial Sequence
<220> FEATURE:
<223> OTHER INFORMATION: primer or probe

<400> SEQUENCE: 16
trttaggtaa tycaactagc acct 24

<210> SEQ ID NO 17

-continued

<211> LENGTH: 24
<212> TYPE: DNA
<213> ORGANISM: Artificial Sequence
<220> FEATURE:
<223> OTHER INFORMATION: primer or probe

<400> SEQUENCE: 17
tgttagataa tccaacyagc acct 24

<210> SEQ ID NO 18
<211> LENGTH: 23
<212> TYPE: DNA
<213> ORGANISM: Artificial Sequence
<220> FEATURE:
<223> OTHER INFORMATION: primer or probe

<400> SEQUENCE: 18
gktargtaat ccaactagca cct 23

<210> SEQ ID NO 19
<211> LENGTH: 24
<212> TYPE: DNA
<213> ORGANISM: Artificial Sequence
<220> FEATURE:
<223> OTHER INFORMATION: primer or probe

<400> SEQUENCE: 19
tgttaggtar tccaactagc ayct 24

<210> SEQ ID NO 20
<211> LENGTH: 24
<212> TYPE: DNA
<213> ORGANISM: Artificial Sequence
<220> FEATURE:
<223> OTHER INFORMATION: primer or probe

<400> SEQUENCE: 20
tgttaggtaa tccaactmgc acyt 24

<210> SEQ ID NO 21
<211> LENGTH: 23
<212> TYPE: DNA
<213> ORGANISM: Artificial Sequence
<220> FEATURE:
<223> OTHER INFORMATION: primer or probe

<400> SEQUENCE: 21
gatggaggac tctatatgct tgt 23

<210> SEQ ID NO 22
<211> LENGTH: 22
<212> TYPE: DNA
<213> ORGANISM: Artificial Sequence
<220> FEATURE:
<223> OTHER INFORMATION: primer or probe

<400> SEQUENCE: 22
atggaggact cgttatgcct gt 22

<210> SEQ ID NO 23
<211> LENGTH: 21
<212> TYPE: DNA
<213> ORGANISM: Artificial Sequence
<220> FEATURE:
<223> OTHER INFORMATION: primer or probe

<400> SEQUENCE: 23
ggaggacccg tatgcttgtg t 21

<210> SEQ ID NO 24
<211> LENGTH: 22
<212> TYPE: DNA
<213> ORGANISM: Artificial Sequence
<220> FEATURE:
<223> OTHER INFORMATION: primer or probe

<400> SEQUENCE: 24
tgctaaatga tggagggctt gt 22

<210> SEQ ID NO 25
<211> LENGTH: 21
<212> TYPE: DNA
<213> ORGANISM: Artificial Sequence
<220> FEATURE:
<223> OTHER INFORMATION: primer or probe

<400> SEQUENCE: 25
gatggaggct cgtatgcttg t 21

<210> SEQ ID NO 26
<211> LENGTH: 23
<212> TYPE: DNA
<213> ORGANISM: Artificial Sequence
<220> FEATURE:
<223> OTHER INFORMATION: primer or probe

<400> SEQUENCE: 26
aaggggtttg tggtgaatcc tta 23

<210> SEQ ID NO 27
<211> LENGTH: 23
<212> TYPE: DNA
<213> ORGANISM: Artificial Sequence
<220> FEATURE:
<223> OTHER INFORMATION: primer or probe

<400> SEQUENCE: 27
cagaaaaata gccgtatgct tgt 23

<210> SEQ ID NO 28
<211> LENGTH: 23
<212> TYPE: DNA
<213> ORGANISM: Artificial Sequence
<220> FEATURE:
<223> OTHER INFORMATION: primer or probe

<400> SEQUENCE: 28
tratggagra cttgtatgct tgt 23

<210> SEQ ID NO 29
<211> LENGTH: 23
<212> TYPE: DNA
<213> ORGANISM: Artificial Sequence
<220> FEATURE:
<223> OTHER INFORMATION: primer or probe

<400> SEQUENCE: 29
tgatggagga ctcgtatgcy tgt 23

<210> SEQ ID NO 30
<211> LENGTH: 23
<212> TYPE: DNA

<213> ORGANISM: Artificial Sequence
<220> FEATURE:
<223> OTHER INFORMATION: primer or probe

<400> SEQUENCE: 30
tgatggarra ctcatatgct tgt 23

<210> SEQ ID NO 31
<211> LENGTH: 23
<212> TYPE: DNA
<213> ORGANISM: Artificial Sequence
<220> FEATURE:
<223> OTHER INFORMATION: primer or probe

<400> SEQUENCE: 31
tgatagagaa cttgtatrct trt 23

<210> SEQ ID NO 32
<211> LENGTH: 23
<212> TYPE: DNA
<213> ORGANISM: Artificial Sequence
<220> FEATURE:
<223> OTHER INFORMATION: primer or probe

<400> SEQUENCE: 32
tgatgaagaa cttrtatrct tgt 23

<210> SEQ ID NO 33
<211> LENGTH: 23
<212> TYPE: DNA
<213> ORGANISM: Artificial Sequence
<220> FEATURE:
<223> OTHER INFORMATION: primer or probe

<400> SEQUENCE: 33
tgatrragga cttgtatgct tgt 23

<210> SEQ ID NO 34
<211> LENGTH: 23
<212> TYPE: DNA
<213> ORGANISM: Artificial Sequence
<220> FEATURE:
<223> OTHER INFORMATION: primer or probe

<400> SEQUENCE: 34
tgatggaaaa cttgtatgct tgt 23

<210> SEQ ID NO 35
<211> LENGTH: 23
<212> TYPE: DNA
<213> ORGANISM: Artificial Sequence
<220> FEATURE:
<223> OTHER INFORMATION: primer or probe

<400> SEQUENCE: 35
tgatggagga cttgtayayt tgt 23

<210> SEQ ID NO 36
<211> LENGTH: 23
<212> TYPE: DNA
<213> ORGANISM: Artificial Sequence
<220> FEATURE:
<223> OTHER INFORMATION: primer or probe

<400> SEQUENCE: 36
tgatggagga cttgtaygct trt 23

-continued

```
<210> SEQ ID NO 37
<211> LENGTH: 23
<212> TYPE: DNA
<213> ORGANISM: Artificial Sequence
<220> FEATURE:
<223> OTHER INFORMATION: primer or probe

<400> SEQUENCE: 37

tgatggagga ctyatatgct trt                                              23


<210> SEQ ID NO 38
<211> LENGTH: 22
<212> TYPE: DNA
<213> ORGANISM: Artificial Sequence
<220> FEATURE:
<223> OTHER INFORMATION: primer or probe

<400> SEQUENCE: 38

gatggaggac tcgtwygctt gt                                               22
```